(12) United States Patent
Barlaam et al.

(10) Patent No.: US 7,521,453 B2
(45) Date of Patent: Apr. 21, 2009

(54) PYRIMIDINE DERIVATIVES AS MODULATORS OF INSULIN-LIKE GROWTH FACTOR-1 RECEPTOR (IGF-I)

(75) Inventors: Bernard Barlaam, Reims (FR); Andrew Pape, Cheshire (GB); Andrew Thomas, Cheshire (GB)

(73) Assignee: AstraZeneca AB, Sodertalje (SE)

( * ) Notice: Subject to any disclaimer, the term of this patent is extended or adjusted under 35 U.S.C. 154(b) by 542 days.

(21) Appl. No.: 10/497,744

(22) PCT Filed: Dec. 3, 2002

(86) PCT No.: PCT/SE02/02221

§ 371 (c)(1), (2), (4) Date: Nov. 8, 2004

(87) PCT Pub. No.: WO03/048133

PCT Pub. Date: Jun. 12, 2003

(65) Prior Publication Data

US 2005/0054638 A1  Mar. 10, 2005

(30) Foreign Application Priority Data

Dec. 7, 2001  (SE)  .................... 0104140

(51) Int. Cl.
C07D 239/48 (2006.01)
C07D 403/12 (2006.01)
A61K 31/505 (2006.01)

(52) U.S. Cl. .................. 514/255.05; 514/275; 544/295; 544/324

(58) Field of Classification Search ............... 544/295, 544/324; 514/255.05, 275
See application file for complete search history.

(56) References Cited

U.S. PATENT DOCUMENTS 4,038,240 A  7/1977 Hugl et al.
5,147,876 A  9/1992 Mizuchi

FOREIGN PATENT DOCUMENTS

| WO | WO-97/09325 | 3/1997 |
|---|---|---|
| WO | 97/19065 A1 | 5/1997 |
| WO | WO-98/38171 | 9/1998 |
| WO | 00/12485 A1 | 3/2000 |
| WO | WO-00/27825 | 5/2000 |
| WO | WO-00/35455 | 6/2000 |
| WO | WO-00/39101 | 7/2000 |
| WO | WO-00/63182 | 10/2000 |
| WO | WO-00/78731 | 12/2000 |
| WO | WO-01/22938 | 4/2001 |
| WO | 01/60816 A1 | 8/2001 |
| WO | 01/64655 A1 | 9/2001 |
| WO | WO-01/64656 | 9/2001 |
| WO | WO-01/85699 | 11/2001 |
| WO | WO-02/22606 | 3/2002 |
| WO | WO-02/50065 | 6/2002 |

OTHER PUBLICATIONS

Simone, Oncology: Introduction, Cecil Textbook of Medicine, 20th Edition, vol. 1, pp. 1004-1010, 1996.*
LeRoith et al., The insulin-like growth factor system and cancer, Cancer Letters, 195 (2003), pp. 127-137.*
Ulrich, Chapter 4: Crystallization, Kirk-Othmer Encyclopedia of Chemical Technology, Aug. 2002.*
Vippagunta et al., Cyrstalline Solids, Advanced Drug Delivery Reviews, 48, pp. 3-26, 2001.*
West, Solid Solutions, Solid State Chemistry and its applications, pp. 358 & 365, 1988.*
El-Kerdawy et al., "2,4-Bis (substituted)-5-nitropyrimidines of expected diuretic action," Egypt. J. Chem. 29(2):247-251 (1986).
Parrizas et al., "Specific inhibition of insulin-like growth factor-1 and insulin receptor tyrosine kinase activity and biological function by tyrphostins," Endocrinology 138(4):1427-1433 (1997).
Breault, Gloria A., et al., "Cyclin-Dependent Kinase 4 Inhibitors as a Treatment for Cancer. Part 2: Identification and Optimisation of Substituted 2,4-Bis Anilino Pyrimidines", Bioorganic & Medicinal Chemistry Letters, 2003, 2961-2966, vol. 13.
Pierce, Albert C. et al., "CH . . . O and CH . . . N Hydrogen Bonds in Ligand Disign: A Novel Quinazolin-4-ylthiazol-2-ylamine Protein Kinase Inhibitor", J. Med. Chem, 2005, 1278-1281, vol. 48.

* cited by examiner

Primary Examiner—Deepak Rao

(57) ABSTRACT

The invention provides compounds of formula

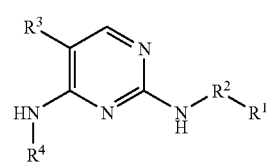

(I)

in which $R^1$, $R^2$, $R^3$ and $R^4$ have the meanings defined in the specification; processes for the preparation; pharmaceutical compositions containing them; a process for preparing the pharmaceutical compositions; and their use in therapy.

18 Claims, No Drawings

PYRIMIDINE DERIVATIVES AS MODULATORS OF INSULIN-LIKE GROWTH FACTOR-1 RECEPTOR (IGF-I)

CROSS-REFERENCE TO RELATED APPLICATIONS

This application is a national stage filing under 35 U.S.C. 371 of International Application No. PCT/SE02/02221, filed Dec. 3, 2002, which claims priority from Sweden Patent Application No. 0104140-9, filed Dec. 7, 2001, the specification of which is incorporated by reference herein. International Application No. PCT/SE02/02221 was published under PCT Article 21(2) in English.

The present invention relates to pyrimidine derivatives, a process for their preparation, pharmaceutical compositions containing them, a process for preparing the pharmaceutical compositions, and their use in therapy.

The insulin-like growth factor (IGF) axis consists of ligands, receptors, binding proteins and proteases. The two ligands, IGF-I and IGF-II, are mitogenic peptides that signal through interaction with the type 1 insulin-like growth factor receptor (IGF-1R), a hetero-tetrameric cell surface receptor. Binding of either ligand stimulates activation of a tyrosine kinase domain in the intracellular region of the β-chain and results in phosphorylation of several tyrosine residues resulting in the recruitment and activation of various signaling molecules. The intracellular domain has been shown to transmit signals for mitogenesis, survival, transformation, and differentiation in cells. The structure and function of the IGF-1R has been reviewed by Adams et al (*Cellular and Molecular Life Sciences*, 57, 1050-1093, 2000). The IGF-IIR (also known as mannose 6-phosphate receptor) has no such kinase domain and does not signal mitogenesis but may act to regulate ligand availability at the cell surface, counteracting the effect of the IGF-1R. The IGF binding proteins (IGFBP) control availability of circulating IGF and release of IGF from these can be mediated by proteolytic cleavage. These other components of the IGF axis have been reviewed by Collett-Solberg and Cohen (*Endocrine*, 12, 121-136, 2000).

There is considerable evidence linking IGF signaling with cellular transformation and the onset and progression of tumours. IGF has been identified as the major survival factor that protects from oncogene induced cell death (Harrington et al, *EMBO J*, 13, 3286-3295, 1994). Cells lacking IGF-1R have been shown to be refractory to transformation by several different oncogenes (including SV40T antigen and ras) that efficiently transform corresponding wild-type cells (Sell et al., *Mol. Cell Biol.*, 14, 3604-12,1994). Upregulation of components of the IGF axis has been described in various tumour cell lines and tissues, particularly tumours of the breast (Surmacz, *Journal of Mammary Gland Biology & Neoplasia*, 5, 95-105, 2000), prostate (Djavan et al, *World J. Urol.*, 19, 225-233, 2001, and O'Brien et al, *Urology*, 58, 1-7, 2001) and colon (Guo et al, *Gastroenterology*, 102, 1101-1108, 1992). Conversely, IGF-IIR has been implicated as a tumour suppressor and is deleted in some cancers (DaCosta et al, *Journal of Mammary Gland Biology & Neoplasia*, 5, 85-94, 2000). There is a growing number of epidemiological studies linking increased circulating IGF (or increased ratio of IGF-1 to IGFBP3) with cancer risk (Yu and Rohan, *J. Natl. Cancer Inst.*, 92, 1472-1489, 2000). Transgenic mouse models also implicate IGF signaling in the onset of tumour cell proliferation (Lamm and Christofori, *Cancer Res.* 58, 801-807, 1998, Foster et al, *Cancer Metas. Rev.*, 17, 317-324, 1998, and DiGiovanni et al, *Proc. Natl. Acad. Sci.*, 97, 3455-3460, 2000).

Several in vitro and in vivo strategies have provided the proof of principal that inhibition of IGF-1R signaling reverses the transformed phenotype and inhibits tumour cell growth. These include neutralizing antibodies (Kalebic et al *Cancer Res.*, 54, 5531-5534, 1994), antisense oligonucleotides (Resnicoff et al, *Cancer Res.*, 54, 2218-2222, 1994), triple-helix forming oligonucleotides (Rinninsland et al, *Proc. Natl. Acad. Sci.*, 94, 5854-5859, 1997), antisense mRNA (Nakamura et al, *Cancer Res.*, 60, 760-765, 2000) and dominant negative receptors (D'Ambrosio et al., *Cancer Res.*, 56, 4013-4020, 1996). Antisense oligonucleotides have shown that inhibition of IGF-1R expression results in induction of apoptosis in cells in vivo (Resnicoff et al, *Cancer Res.*, 55, 2463-2469, 1995) and have been taken into man (Resnicoff et al, *Proc. Amer. Assoc. Cancer Res.*, 40 Abs 4816, 1999). However, none of these approaches is particularly attractive for the treatment of major solid tumour disease.

Since increased IGF signaling is implicated in the growth and survival of tumour cells, and bloking IGF-1R function can reverse this, inhibition of the IGF-1R tyrosine kinase domain is an appropriate therapy by which to treat cancer. In vitro and in vivo studies with the use of dominant-negative IGF-1R variants support this. In particular, a point mutation in the ATP binding site which blocks receptor tyrosine kinase activity has proved effective in preventing tumour cell growth (Kulik et al, *Mol. Cell. Biol.*, 17, 1595-1606, 1997). Several pieces of evidence imply that normal cells are less susceptible to apoptosis caused by inhibition of IGF signaling, indicating that a therapeutic margin is possible with such treatment (Baserga, *Trends Biotechnol.*, 14, 150-2,1996).

There are few reports of selective IGF-1R tyrosine kinase inhibitors. Parrizas et al. described tyrphostins that had some efficacy in vitro and in vivo (Parrizas et al., *Endocrinology*, 138:1427-33 (1997)). These compounds were of modest potency and selectivity over the insulin receptor. Telik Inc. have described heteroaryl-aryl ureas which have selectivity over insulin receptors but potency against tumour cells in vitro is still modest (Published PCT Patent Application No. WO 00/35455).

In accordance with the present invention, there is provided a compound of formula (I):

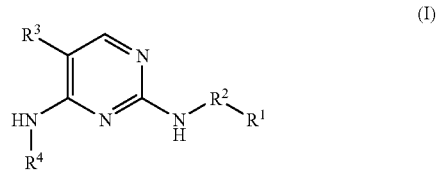

wherein $R^1$ represents a 5- or 6-membered heteroaromatic ring comprising at least one ring heteroatom selected from nitrogen, oxygen and sulphur, the ring being optionally substituted by at least one substituent selected from $C_1$-$C_6$alkyl, $C_1$-$C_6$alkoxy (each of which may be optionally substituted by at least one substituent selected from halogen, amino (—$NH_2$), hydroxyl and trifluoromethyl), halogen, nitro, cyano, —$NR^5R^6$, carboxyl, hydroxyl, $C_2$-$C_6$alkenyl, $C_3$-$C_6$cycloalkyl, $C_1$-$C_6$alkoxycarbonyl, $C_1$-$C_6$alkylcarbonyl, $C_1$-$C_6$alkylcarbonylamino, phenylcarbonyl, —$S(O)_mC_1$-$C_6$alkyl, —$C(O)NR^7R^8$, —$SO_2NR^{7a}R^{8a}$, and an unsaturated 5- to 6-membered ring which may comprise at least one ring heteroatom selected from nitrogen, oxygen and sulphur, the ring itself being optionally substituted by at least one substituent selected from $C_1$-$C_6$alkyl, $C_1$-$C_6$alkoxy (each of which may be optionally substituted by at least one substituent selected from halogen, amino (—$NH_2$), hydroxyl and trifluoromethyl), halogen, nitro, cyano, —$NR^9R^{10}$, carboxyl, hydroxyl, $C_2$-$C_6$alkenyl, $C_3$-$C_6$cycloalkyl, $C_1$-$C_6$alkoxycarbonyl, $C_1$-$C_6$alkylcarbonyl, $C_1$-$C_6$alkylcarbonylamino, phenylcarbonyl, —$S(O)_nC_1$-$C_6$alkyl, —$C(O)NR^{11}R^{12}$ and —$SO_2NR^{11a}R^{12a}$;

m is 0, 1 or 2;

n is 0, 1 or 2;

$R^2$ represents a $C_1$-$C_4$alkyl group optionally substituted by at least one substituent selected from halogen, hydroxyl and $C_1$-$C_3$alkoxy;

$R^3$ represents hydrogen, halogen or trifluoromethyl;

$R^4$ represents a 5-membered heteroaromatic ring comprising at least one ring heteroatom selected from nitrogen, oxygen and sulphur, the ring being optionally substituted by at least one substituent selected from $C_1$-$C_6$alkyl, $C_1$-$C_6$alkoxy (each of which may be optionally substituted by at least one substituent selected from halogen, amino (—$NH_2$), hydroxyl and trifluoromethyl), halogen, nitro, cyano, —$NR^{13}R^{14}$, carboxyl, hydroxyl, $C_2$-$C_6$alkenyl, $C_3$-$C_6$cycloalkyl, $C_1$-$C_4$alkoxycarbonyl, $C_1$-$C_4$alkylcarbonyl, $C_1$-$C_4$alkylcarbonylamino, phenylcarbonyl, —$S(O)_pC_1$-$C_4$alkyl, —$C(O)NR^{15}R^{16}$ and —$SO_2NR^{15a}R^{16a}$;

p is 0, 1 or 2;

$R^5$ and $R^6$ each independently represent hydrogen, $C_1$-$C_4$alkyl or $C_3$-$C_6$cycloalkyl, or $R^5$ and $R^6$ together with the nitrogen atom to which they are attached form a 4- to 6-membered saturated heterocycle;

$R^7$ and $R^8$ each independently represent hydrogen, $C_1$-$C_4$alkyl or $C_3$-$C_6$cycloalkyl, or $R^7$ and $R^8$ together with the nitrogen atom to which they are attached form a 4- to 6-membered saturated heterocycle;

$R^{7a}$ and $R^{8a}$ each independently represent hydrogen, $C_1$-$C_4$alkyl or $C_3$-$C_6$cycloalkyl, or $R^{7a}$ and $R^{8a}$ together with the nitrogen atom to which they are attached form a 4- to 6-membered saturated heterocycle;

$R^9$ and $R^{10}$ each independently represent hydrogen, $C_1$-$C_4$alkyl or $C_3$-$C_6$cycloalkyl, or $R^9$ and $R^{10}$ together with the nitrogen atom to which they are attached form a 4- to 6-membered saturated heterocycle;

$R^{11}$ and $R^{12}$ each independently represent hydrogen, $C_1$-$C_4$alkyl or $C_3$-$C_6$cycloalkyl, or $R^{11}$ and $R^{12}$ together with the nitrogen atom to which they are attached form a 4- to 6-membered saturated heterocycle;

$R^{11a}$ and $R^{12a}$ each independently represent hydrogen, $C_1$-$C_4$alkyl or $C_3$-$C_6$cycloalkyl, or $R^{11a}$ and $R^{12a}$ together with the nitrogen atom to which they are attached form a 4- to 6-membered saturated heterocycle;

$R^{13}$ and $R^{14}$ each independently represent hydrogen, $C_1$-$C_4$alkyl or $C_3$-$C_6$cycloalkyl, or $R^{13}$ and $R^{14}$ together with the nitrogen atom to which they are attached form a 4- to 6-membered saturated heterocycle;

$R^{15}$ and $R^{16}$ each independently represent hydrogen, $C_1$-$C_4$alkyl or $C_3$-$C_6$cycloalkyl, or $R^5$ and $R^{16}$ together with the nitrogen atom to which they are attached form a 4- to 6-membered saturated heterocycle; and $R^{15a}$ and $R^{16a}$ each independently represent hydrogen, $C_1$-$C_4$alkyl or $C_3$-$C_6$cycloalkyl, or $R^{15a}$ and $R^{16a}$ together with the nitrogen atom to which they are attached form a 4- to 6-membered saturated heterocycle;

or a pharmaceutically acceptable salt or solvate thereof.

In the context of the present specification, unless otherwise indicated, an alkyl substituent group or an alkyl moiety in a substituent group may be linear or branched. When $R^5$ and $R^6$, or $R^7$ and $R^8$, or $R^{7a}$ and $R^8$, or $R^9$ and $R^{10}$, or $R^{11}$ and $R^{12}$, or $R^{11a}$ and $R^{12a}$, or $R^{13}$ and $R^4$, or $R^{15}$ and $R^6$, or $R^{15a}$ and $R^{16a}$ represent a saturated heterocycle, it should be understood that the only heteroatom present is the nitrogen atom to which $R^5$ and $R^6$, or $R^7$ and $R^8$, or $R^{7a}$ and $R^{8a}$, or $R^9$ and $R^{10}$, or $R^{11}$ and $R^{12}$, or $R^{11a}$ and $R^{12a}$, or $R^{13}$ and $R^{14}$, or $R^{15}$ and $R^{16}$, or $R^{15a}$ and $R^{16a}$ are attached. In the definition of $R^1$, it should be noted that the unsaturated 5- to 6-membered ring may have alicyclic or aromatic properties.

Examples of "$C_1$-$C_6$alkyl" and "$C_1$-$C_4$alkyl" include methyl, ethyl, isopropyl and t-butyl. Examples of "$C_1$-$C_6$alkoxycarbonyl" include methoxycarbonyl, ethoxycarbonyl, n- and t-butoxycarbonyl. Examples of "$C_1$-$C_6$alkoxy" and "$C_1$-$C_3$alkoxy" include methoxy, ethoxy and propoxy. Examples of "$C_1$-$C_6$alkylcarbonylamino" include formamido, acetamido and propionylamino. Examples of "$S(O)_m C_1$-$C_6$alkyl" wherein m is 0 to 2 include methylthio, ethylthio, methylsulphinyl, ethylsulphinyl, mesyl and ethylsulphonyl. Examples of "$C_1$-$C_6$alkylcarbonyl" include propionyl and acetyl. Examples of "$C_2$-$C_6$alkenyl" are vinyl, allyl and 1-propenyl. Examples of "$C_3$-$C_6$cycloalkyl" are cyclopropyl, cyclopentyl and cyclohexyl.

A "5- or 6-membered heteroaromatic ring comprising at least one ring heteroatom selected from nitrogen, oxygen and sulphur" is a fully unsaturated, aromatic monocyclic ring containing 5 or 6 atoms of which at least one is a heteroatom selected from nitrogen, oxygen and sulphur, which may, unless otherwise specified, be carbon or nitrogen linked. Suitably a "5- or 6-membered heteroaromatic ring comprising at least one ring heteroatom selected from nitrogen, oxygen and sulphur" is pyridyl, imidazolyl, isoxazolyl, pyrazolyl, furyl, pyrazinyl, pyridazinyl, pyrimidinyl, pyrrolyl or thienyl.

An "unsaturated 5- to 6-membered ring which may comprise at least one ring heteroatom selected from nitrogen, oxygen and sulphur" is a fully or partially unsaturated, monocyclic ring containing 5 or 6 atoms optionally of which at least one is a heteroatom selected from nitrogen, oxygen and sulphur, and which may, unless otherwise specified, be carbon or nitrogen linked. Suitably an "unsaturated 5- to 6-membered ring which may comprise at least one ring heteroatom selected from nitrogen, oxygen and sulphur" is phenyl or pyridyl.

A "5-membered heteroaromatic ring comprising at least one ring heteroatom selected from nitrogen, oxygen and sulphur" is a fully unsaturated, aromatic monocyclic ring containing 5 atoms of which at least one is a heteroatom selected from nitrogen, oxygen and sulphur, which may, unless otherwise specified, be carbon or nitrogen linked. Suitably a "5-membered heteroaromatic ring comprising at least one ring heteroatom selected from nitrogen, oxygen and sulphur" is pyrazolyl.

$R^1$ represents an optionally substituted 5- or 6-membered heteroaromatic ring comprising at least one ring heteroatom (e.g. one, two, three or four ring heteroatoms independently) selected from nitrogen, oxygen and sulphur. Examples of heteroaromatic rings include thienyl (e.g. 3-thienyl), pyrazolyl (e.g. 4-pyrazolyl), isoxazolyl (e.g. 5-isoxazolyl), thiadiazolyl, pyrrolyl (e.g. 2-pyrrolyl), furanyl (2- or 3-furanyl), thiazolyl, triazolyl, tetrazolyl, imidazolyl (e.g. 4-imidazolyl), pyrazinyl (e.g. 2-pyrazinyl), pyridazinyl (e.g. 3-pyridazinyl), pyrimidinyl (e.g. 4- or 5-pyrimidinyl) and pyridyl (2-, 3- or 4-pyridyl).

In $R^1$, the 5- or 6-membered heteroaromatic ring is optionally substituted by at least one substituent (e.g. one, two, three or four substituents independently) selected from $C_1$-$C_6$, particularly $C_1$-$C_4$alkyl (such as methyl, ethyl, n-propyl, isopropyl, n-butyl, isobutyl, tert-butyl, n-pentyl or n-hexyl), $C_1$-$C_6$, particularly $C_1$-$C_4$alkoxy (such as methoxy, ethoxy, n-propoxy, n-butoxy, tert-butoxy, n-pentoxy or n-hexoxy) (each of the $C_1$-$C_6$alkyl and $C_1$-$C_6$alkoxy substituent groups being optionally substituted by at least one substituent, e.g. one, two, three or four substituents independently, selected from halogen (such as fluorine, chlorine bromine or iodine), amino, hydroxyl and trifluoromethyl), halogen (such as fluorine, chlorine, bromine or iodine), nitro, cyano, —NR$^5$R$^6$, carboxyl, hydroxyl, $C_2$-$C_6$, particularly $C_2$-$C_4$alkenyl (such as ethenyl), $C_3$-$C_6$cycloalkyl (cyclopropyl, cyclobutyl, cyclopentyl and cyclohexyl), $C_1$-$C_6$, particularly $C_1$-$C_4$alkoxycarbonyl (such as methoxycarbonyl or ethoxycarbonyl), $C_1$-$C_6$, particularly $C_1$-$C_4$alkylcarbonyl (such as methylcarbonyl, ethylcarbonyl, n-propylcarbonyl, isopropylcarbonyl, n-butylcarbonyl, n-pentylcarbonyl or n-hexylcarbonyl), $C_1$-$C_6$, particularly $C_1$-$C_4$alkylcarbonylamino (such as methylcarbonylamino or ethylcarbonylamino), phenylcarbonyl, —S(O)$_m$C$_1$-$C_6$, particularly $C_1$-$C_4$alkyl, —C(O)NR$^7$R$^8$, —SO$_2$NR$^{7a}$R$^{8a}$, and an optionally substituted unsaturated 5- to 6-membered ring which may comprise at least one ring heteroatom (e.g. one, two, three or four ring heteroatoms independently) selected from nitrogen, oxygen and sulphur.

Examples of the unsaturated 5- to 6-membered ring include phenyl, cylopentenyl, cyclohexenyl, thienyl (e.g. 3-thienyl), pyrazolyl (e.g. 4-pyrazolyl), isoxazolyl (e.g. 5-isoxazolyl), thiadiazolyl, pyrrolyl (e.g. 2-pyrrolyl), furanyl (2- or 3-furanyl), thiazolyl, triazolyl, tetrazolyl, imidazolyl (e.g. 4-imidazolyl), pyrazinyl (e.g. 2-pyrazinyl), pyridazinyl (e.g. 3-pyridazinyl), pyrimidinyl (e.g. 4- or 5-pyrimidinyl) and pyridyl (2-, 3- or 4-pyridyl). The ring may itself be optionally substituted by at least one substituent (e.g. one, two, three or four substituents independently) selected from $C_1$-$C_6$, particularly $C_1$-$C_4$alkyl (such as methyl, ethyl, n-propyl, isopropyl, n-butyl, isobutyl, tert-butyl, n-pentyl or n-hexyl), $C_1$-$C_6$, particularly $C_1$-$C_4$alkoxy (such as methoxy, ethoxy, n-propoxy, n-butoxy, tert-butoxy, n-pentoxy or n-hexoxy) (each of the $C_1$-$C_6$alkyl and $C_1$-$C_6$alkoxy substituent groups being optionally substituted by at least one substituent, e.g. one, two, three or four substituents independently, selected from halogen (such as fluorine, chlorine bromine or iodine), amino, hydroxyl and trifluoromethyl), halogen (such as fluorine, chlorine, bromine or iodine), nitro, cyano, —NR$^9$R$^{10}$, carboxyl, hydroxyl, $C_2$-$C_6$, particularly $C_2$-$C_4$alkenyl (such as ethenyl), $C_3$-$C_6$cycloalkyl (cyclopropyl, cyclobutyl, cyclopentyl and cyclohexyl), $C_1$-$C_6$, particularly $C_1$-$C_4$alkoxycarbonyl (such as methoxycarbonyl or ethoxycarbonyl), $C_1$-$C_6$, particularly $C_1$-$C_4$alkylcarbonyl (such as methylcarbonyl, ethylcarbonyl, n-propylcarbonyl, isopropylcarbonyl, n-butylcarbonyl, n-pentylcarbonyl or n-hexylcarbonyl), $C_1$-$C_6$, particularly $C_1$-$C_4$alkylcarbonylamino (such as methylcarbonylamino or ethylcarbonylamino), phenylcarbonyl, —S(O)$_n$C$_1$-$C_6$, particularly $C_1$-$C_4$alkyl, —C(O)NR$^{11}$R$^{12}$ and —SO$_2$NR$^{11a}$R$^{12a}$.

Particular values of variable groups are as follows. Such values may be used where appropriate with any of the definitions, claims or embodiments defined hereinbefore or hereinafter.

In one embodiment of the invention, R$^1$ represents a 5- or 6-membered heteroaromatic ring comprising one or two ring heteroatoms selected from nitrogen and oxygen, the ring being optionally substituted by at least one substituent selected from $C_1$-$C_6$alkyl, $C_1$-$C_6$alkoxy, halogen, nitro, cyano, —NR$^5$R$^6$, carboxyl, hydroxyl, $C_2$-$C_6$alkenyl, $C_3$-$C_6$cycloalkyl, $C_1$-$C_6$alkoxycarbonyl, $C_1$-$C_6$alkylcarbonyl, $C_1$-$C_6$alkylcarbonylamino, phenylcarbonyl, —S(O)$_m$C$_1$-$C_6$alkyl, —C(O)NR$^7$R$^8$, —SO$_2$NR$^{7a}$R$^{8a}$, and an unsaturated 6-membered ring which may comprise one ring nitrogen atom, the ring itself being optionally substituted by at least one substituent selected from $C_1$-$C_6$alkyl, $C_1$-$C_6$alkoxy, halogen, nitro, cyano, —NR$^9$R$^{10}$, carboxyl, hydroxyl, $C_2$-$C_6$alkenyl, $C_3$-$C_6$cycloalkyl, $C_1$-$C_6$alkoxycarbonyl, $C_1$-$C_6$alkylcarbonyl, $C_1$-$C_6$alkylcarbonylamino, phenylcarbonyl, —S(O)$_n$C$_1$-$C_6$alkyl, —C(O)NR$^{11}$R$^{12}$ and —SO$_2$NR$^{11a}$R$^{12a}$.

In a further embodiment of the invention, R$^1$ represents a 5- or 6-membered heteroaromatic ring comprising one or two ring heteroatoms selected from nitrogen and oxygen, the ring being optionally substituted by at least one substituent selected from $C_1$-$C_6$alkyl, $C_1$-$C_6$alkoxy, halogen, phenyl and pyridyl, each of the phenyl and pyridyl substituent groups itself being optionally substituted by at least one substituent selected from $C_1$-$C_6$alkyl, $C_1$-$C_6$alkoxy and halogen.

In an additional aspect R$^1$ represents a 5- or 6-membered heteroaromatic ring comprising at least one ring heteroatom selected from nitrogen, oxygen and sulphur, the ring being optionally substituted by at least one substituent selected from $C_1$-$C_6$alkyl, $C_1$-$C_6$alkoxy (each of which may be optionally substituted by at least one substituent selected from hydroxyl), halogen, —C(O)NR$^7$R$^8$, $C_1$-$C_6$alkoxycarbonyl, and an unsaturated 5- to 6-membered ring which may comprise at least one ring heteroatom selected from nitrogen and oxygen, the ring itself being optionally substituted by at least one substituent selected from $C_1$-$C_6$alkyl, $C_1$-$C_6$alkoxy (each of which may be optionally substituted by at least one substituent selected from halogen), halogen and cyano; wherein R$^7$ and R$^8$ are both hydrogen or R$^7$ and R$^8$ together with the nitrogen atom to which they are attached form a 4- to 6-membered saturated heterocycle.

In a further additional aspect R$^1$ represents pyridyl, imidazolyl, isoxazolyl, pyrazolyl, furyl, pyrazinyl, pyridazinyl, pyrimidinyl, pyrrolyl or thienyl; said pyridyl, imidazolyl, isoxazolyl, pyrazolyl, furyl, pyrazinyl, pyridazinyl, pyrimidinyl, pyrrolyl and thienyl being optionally substituted by at least one substituent selected from methyl, isopropyl, hydroxymethyl, methoxy, chloro, bromo, carbamoyl, methoxycarbonyl, pyrrolidin-1-ylcarbonyl, phenyl and pyridyl; said phenyl or pyridyl being optionally substituted by at least one substituent selected from methyl, trifluoromethyl, methoxy, ethoxy, trifluoromethoxy, fluoro, chloro, bromo and cyano.

In a further additional aspect R$^1$ represents pyrid-2-yl, pyrid-3-yl, pyrid-4-yl, 2-methoxypyrid-5-yl, 2-cyanopyrid-5-yl, 3-bromopyrid-5-yl, 3-(pyrid-2-yl)pyrid-5-yl, 4-(pyrid-2-yl)pyrid-2-yl, 3-chloropyrid-2-yl, 3-methylpyrid-2-yl, 6-methylpyrid-2-yl, 5,6-dimethylpyrid-2-yl, imidazol-4-yl, imidazol-5-yl, 3-methylisoxazol-5-yl, 5-methylisoxazol-3-yl, 3-isopropylisoxazol-5-yl, 3-methoxycarbonylisoxazol-5-yl, 3-(hydroxymethyl)isoxazol-5-yl, 3-carbamoylisoxazol-5-yl, 3-(pyrrolidin-1-ylcarbonyl)isoxazol-5-yl, 3-phenylisoxazol-5-yl, 3-(pyrid-2-yl)isoxazol-5-yl, 3-(2-methoxypyrid-3-yl)isoxazol-5-yl, 3-(2-methoxyphenyl) isoxazol-5-yl, 3-(3-methoxyphenyl)isoxazol-5-yl, 3-(2-ethoxyphenyl)isoxazol-5-yl, 3-(2-trifluoromethylphenyl) isoxazol-5-yl, 3-(2-trifluoromethoxyphenyl)isoxazol-5-yl, 3-(2-chlorophenyl)isoxazol-5-yl, 3-(2-bromophenyl)isoxazol-5-yl, 3-(2-methylphenyl)isoxazol-5-yl, 3-(2-fluorophenyl)isoxazol-5-yl, 3-(2-cyanophenyl)isoxazol-5-yl, 5-methylpyrazol-4-yl, fur-2-yl, fur-3-yl, 5-methylfur-2-yl, pyrazin-2-yl, 2-methylpyrazin-5-yl, pyridazin-3-yl, pyrimidin-4-yl, 1-methylpyrrol-2-yl and thien-3-yl.

R$^2$ represents a $C_1$-$C_4$alkyl group (such as methyl, ethyl, n-propyl, isopropyl, n-butyl, isobutyl or tert-butyl) optionally substituted by at least one substituent (e.g. one, two, three or four substituents independently) selected from halogen (e.g. fluorine, chlorine, bromine or iodine), hydroxyl and $C_1$-$C_3$alkoxy (e.g. methoxy, ethoxy and n-propoxy).

In one embodiment of the invention, $R^2$ represents $CH_2$ or $(CH_2)_2$.

In a further embodiment $R^2$ represents a $C_1$-$C_4$alkyl group.

In an additional embodiment $R^2$ represents methyl, ethyl and propyl.

$R^3$ represents hydrogen, halogen (e.g. fluorine, chlorine, bromine or iodine) or trifluoromethyl.

In one embodiment of the invention, $R^3$ represents chlorine or bromine.

In a further embodiment $R^3$ represents hydrogen or halogen.

In an additional embodiment $R^3$ represents hydrogen, chloro or bromo.

$R^4$ represents an optionally substituted 5-membered heteroaromatic ring comprising at least one ring heteroatom (e.g. one, two, three or four ring heteroatoms independently) selected from nitrogen, oxygen and sulphur. Examples of rings include thienyl (e.g. 3-thienyl), pyrazolyl (e.g. 4-pyrazolyl), isoxazolyl (e.g. 5-isoxazolyl), thiadiazolyl, pyrrolyl (e.g. 2-pyrrolyl), furanyl (2- or 3-furanyl), thiazolyl, triazolyl, tetrazolyl, imidazolyl (e.g. 4-imidazolyl).

The 5-membered heteroaromatic ring in $R^4$ is optionally substituted by at least one substituent (e.g. one, two, three or four substituents independently) selected from $C_1$-$C_6$, particularly $C_1$-$C_4$alkyl (such as methyl, ethyl, n-propyl, isopropyl, n-butyl, isobutyl, tert-butyl, n-pentyl or n-hexyl), $C_1$-$C_6$, particularly $C_1$-$C_4$alkoxy (such as methoxy, ethoxy, n-propoxy, n-butoxy, tert-butoxy, n-pentoxy or n-hexoxy) (each of the $C_1$-$C_6$alkyl and $C_1$-$C_6$alkoxy substituent groups being optionally substituted by at least one substituent, e.g. one, two, three or four substituents independently, selected from halogen (such as fluorine, chlorine bromine or iodine), amino, hydroxyl and trifluoromethyl), halogen (such as fluorine, chlorine, bromine or iodine), nitro, cyano, —$NR^{13}R^{14}$, carboxyl, hydroxyl, $C_2$-$C_6$, particularly $C_2$-$C_4$alkenyl (such as ethenyl), $C_3$-$C_6$cycloalkyl (cyclopropyl, cyclobutyl, cyclopentyl and cyclohexyl), $C_1$-$C_4$, particularly $C_1$-$C_3$alkoxycarbonyl (such as methoxycarbonyl or ethoxycarbonyl), $C_1$-$C_4$, particularly $C_1$-$C_3$alkylcarbonyl (such as methylcarbonyl, ethylcarbonyl, n-propylcarbonyl, isopropylcarbonyl or n-butylcarbonyl), $C_1$-$C_4$, particularly $C_1$-$C_3$alkylcarbonylamino (such as methylcarbonylamino or ethylcarbonylamino), phenylcarbonyl, —$S(O)_pC_1$-$C_4$, particularly $C_1$-$C_2$alkyl, —$C(O)NR^{15}R^{16}$ and —$SO_2NR^{5a}R^{16a}$.

In one embodiment of the invention, $R^4$ represents a 5-membered heteroaromatic ring comprising one or two ring heteroatoms selected from nitrogen and oxygen, the ring being optionally substituted by at least one substituent selected from $C_1$-$C_6$alkyl, $C_1$-$C_6$alkoxy, halogen, nitro, cyano, —$NR^3R^4$, carboxyl, hydroxyl, $C_2$-$C_6$alkenyl, $C_3$-$C_6$cycloalkyl, $C_1$-$C_4$alkoxycarbonyl, $C_1$-$C_4$alkylcarbonyl, $C_1$-$C_4$alkylcarbonylamino, phenylcarbonyl, —$S(O)_pC_1$-$C_4$alkyl, —$C(O)NR^{16}$ and —$SO_2NR^{15a}R^{16a}$.

In a further embodiment of the invention, $R^4$ represents a 5-membered heteroaromatic ring comprising two ring nitrogen atoms, the ring being optionally substituted by at least one substituent selected from $C_1$-$C_6$alkyl, $C_1$-$C_6$alkoxy, halogen and $C_3$-$C_6$cycloalkyl.

In an additional embodiment $R^4$ represents a 5-membered heteroaromatic ring comprising at least one ring heteroatom selected from nitrogen, the ring being optionally substituted by at least one substituent selected from $C_1$-$C_6$alkyl and $C_3$-$C_6$cycloalkyl.

In an additional further embodiment $R^4$ represents pyrazolyl, the ring being optionally substituted by at least one substituent selected from methyl, ethyl, isopropyl, propyl, t-butyl and cyclopropyl.

In another further embodiment $R^4$ represents 5-methylpyrazol-3-yl, 5-ethylpyrazol-3-yl, 5-isopropylpyrazol-3-yl, 5-propylpyrazol-3-yl, 5-t-butylpyrazol-3-yl and 5-cyclopropylpyrazol-3-yl.

$R^5$ and $R^6$ each independently represent hydrogen, $C_1$-$C_4$, particularly $C_1$-$C_2$alkyl (such as methyl, ethyl, n-propyl, isopropyl, n-butyl, isobutyl or tert-butyl) or $C_3$-$C_6$cycloalkyl (cyclopropyl, cyclobutyl, cyclopentyl and cyclohexyl), or $R^5$ and $R^8$ together with the nitrogen atom to which they are attached form a 4- to 6-membered saturated heterocycle (such as pyrrolidinyl or piperidinyl).

$R^7$ and $R^8$ each independently represent hydrogen, $C_1$-$C_4$, particularly $C_1$-$C_2$alkyl (such as methyl, ethyl, n-propyl, isopropyl, n-butyl, isobutyl or tert-butyl) or $C_3$-$C_6$cycloalkyl (cyclopropyl, cyclobutyl, cyclopentyl and cyclohexyl), or $R^7$ and $R^8$ together with the nitrogen atom to which they are attached form a 4- to 6-membered saturated heterocycle (such as pyrrolidinyl or piperidinyl).

$R^{7a}$ and $R^{8a}$ each independently represent hydrogen, $C_1$-$C_4$, particularly $C_1$-$C_2$alkyl (such as methyl, ethyl, n-propyl, isopropyl, n-butyl, isobutyl or tert-butyl) or $C_3$-$C_6$cycloalkyl (cyclopropyl, cyclobutyl, cyclopentyl and cyclohexyl), or $R^{7a}$ and $R^{8a}$ together with the nitrogen atom to which they are attached form a 4- to 6-membered saturated heterocycle (such as pyrrolidinyl or piperidinyl).

$R^9$ and $R^{10}$ each independently represent hydrogen, $C_1$-$C_4$, particularly $C_1$-$C_2$alkyl (such as methyl, ethyl, n-propyl, isopropyl, n-butyl, isobutyl or tert-butyl) or $C_3$-$C_6$cycloalkyl (cyclopropyl, cyclobutyl, cyclopentyl and cyclohexyl), or $R^9$ and $R^{10}$ together with the nitrogen atom to which they are attached form a 4- to 6-membered saturated heterocycle (such as pyrrolidinyl or piperidinyl).

$R^{11}$ and $R^{12}$ each independently represent hydrogen, $C_1$-$C_4$, particularly $C_1$-$C_2$alkyl (such as methyl, ethyl, n-propyl, isopropyl, n-butyl, isobutyl or tert-butyl) or $C_3$-$C_6$cycloalkyl (cyclopropyl, cyclobutyl, cyclopentyl and cyclohexyl), or $R^{11}$ and $R^{12}$ together with the nitrogen atom to which they are attached form a 4- to 6-membered saturated heterocycle (such as pyrrolidinyl or piperidinyl).

$R^{11a}$ and $R^{12a}$ each independently represent hydrogen, $C_1$-$C_4$, particularly $C_1$-$C_2$alkyl (such as methyl, ethyl, n-propyl, isopropyl, n-butyl, isobutyl or tert-butyl) or $C_3$-$C_6$cycloalkyl (cyclopropyl, cyclobutyl, cyclopentyl and cyclohexyl), or $R^{11a}$ and $R^{12a}$ together with the nitrogen atom to which they are attached form a 4- to 6-membered saturated heterocycle (such as pyrrolidinyl or piperidinyl).

$R^{13}$ and $R^{14}$ each independently represent hydrogen, $C_1$-$C_4$, particularly $C_1$-$C_2$alkyl (such as methyl, ethyl, n-propyl, isopropyl, n-butyl, isobutyl or tert-butyl) or $C_3$-$C_6$cycloalkyl (cyclopropyl, cyclobutyl, cyclopentyl and cyclohexyl), or $R^{13}$ and $R^{14}$ together with the nitrogen atom to which they are attached form a 4- to 6-membered saturated heterocycle (such as pyrrolidinyl or piperidinyl).

$R^{15}$ and $R^{16}$ each independently represent hydrogen, $C_1$-$C_4$, particularly $C_1$-$C_2$alkyl (such as methyl, ethyl, n-propyl, isopropyl, n-butyl, isobutyl or tert-butyl) or $C_3$-$C_6$cycloalkyl (cyclopropyl, cyclobutyl, cyclopentyl and cyclohexyl), or $R^{15}$ and $R^{16}$ together with the nitrogen atom to which they are attached form a 4- to 6-membered saturated heterocycle (such as pyrrolidinyl or piperidinyl).

$R^{15a}$ and $R^{16a}$ each independently represent hydrogen, $C_1$-$C_4$, particularly $C_1$-$C_2$alkyl (such as methyl, ethyl, n-propyl, isopropyl, n-butyl, isobutyl or tert-butyl) or $C_3$-$C_6$cycloalkyl (cyclopropyl, cyclobutyl, cyclopentyl and cyclohexyl), or $R^{15a}$ and $R^{16a}$ together with the nitrogen atom to which they are attached form a 4- to 6-membered saturated heterocycle (such as pyrrolidinyl or piperidinyl).

In an embodiment of the invention, there is provided a subset of compounds of formula (I), and pharmaceutically acceptable salts and solvates thereof, in which:

$R^1$ represents a 5- or 6-membered heteroaromatic ring comprising one or two ring heteroatoms selected from nitrogen and oxygen, the ring being optionally substituted by at least one substituent selected from $C_1$-$C_3$alkyl, pyridyl, and phenyl optionally substituted by methoxy;

$R^2$ represents a $C_1$-$C_2$alkyl group;

$R^3$ represents chlorine or bromine; and $R^4$ represents pyrazolyl substituted by at least one substituent selected from $C_1$-$C_4$alkyl and cyclopropyl.

In a further aspect of the invention, there is provided a compound of formula (I) (as depicted above) wherein:

$R^1$ represents a 5- or 6-membered heteroaromatic ring comprising at least one ring heteroatom selected from nitrogen, oxygen and sulphur, the ring being optionally substituted by at least one substituent selected from $C_1$-$C_6$alkyl, $C_1$-$C_6$alkoxy (each of which may be optionally substituted by at least one substituent selected from hydroxyl), halogen, —C(O)NR$^7$R$^8$, $C_1$-$C_6$alkoxycarbonyl, and an unsaturated 5- to 6-membered ring which may comprise at least one ring heteroatom selected from nitrogen and oxygen, the ring itself being optionally substituted by at least one substituent selected from $C_1$-$C_6$alkyl, $C_1$-$C_6$alkoxy (each of which may be optionally substituted by at least one substituent selected from halogen), halogen and cyano; wherein $R^7$ and $R^8$ are both hydrogen or $R^7$ and $R^8$ together with the nitrogen atom to which they are attached form a 4- to 6-membered saturated heterocycle;

$R^2$ represents a $C_1$-$C_4$alkyl group;

$R^3$ represents hydrogen or halogen; and $R^4$ represents a 5-membered heteroaromatic ring comprising at least one ring heteroatom selected from nitrogen, the ring being optionally substituted by at least one substituent selected from $C_1$-$C_6$alkyl and $C_3$-$C_6$cycloalkyl;

or a pharmaceutically acceptable salt or solvate thereof.

In an additional aspect of the invention, there is provided a compound of formula (I) (as depicted above) wherein:

$R^1$ represents pyrid-2-yl, pyrid-3-yl, pyrid-4-yl, 2-methoxypyrid-5-yl, 2-cyanopyrid-5-yl, 3-bromopyrid-5-yl, 3-(pyrid-2-yl)pyrid-5-yl, 4-(pyrid-2-yl)pyrid-2-yl, 3-chloropyrid-2-yl, 3-methylpyrid-2-yl, 6-methylpyrid-2-yl, 5,6-dimethylpyrid-2-yl, imidazol-4-yl, imidazol-5-yl, 3-methylisoxazol-5-yl, 5-methylisoxazol-3-yl, 3-isopropylisoxazol-5-yl, 3-methoxycarbonylisoxazol-5-yl, 3-(hydroxymethyl)isoxazol-5-yl, 3-carbamoylisoxazol-5-yl, 3-(pyrrolidin-1-ylcarbonyl)isoxazol-5-yl, 3-phenylisoxazol-5-yl, 3-(pyrid-2-yl)isoxazol-5-yl, 3-(2-methoxypyrid-3-yl) isoxazol-5-yl, 3-(2-methoxyphenyl)isoxazol-5-yl, 3-(3-methoxyphenyl)isoxazol-5-yl, 3-(2-ethoxyphenyl)isoxazol-5-yl, 3-(2-trifluoromethylphenyl)isoxazol-5-yl, 3-(2-trifluoromethoxyphenyl)isoxazol-5-yl, 3-(2-chlorophenyl) isoxazol-5-yl, 3-(2-bromophenyl)isoxazol-5-yl, 3-(2-methylphenyl)isoxazol-5-yl, 3-(2-fluorophenyl)isoxazol-5-yl, 3-(2-cyanophenyl)isoxazol-5-yl, 5-methylpyrazol-4-yl, fur-2-yl, fur-3-yl, 5-methylfur-2-yl, pyrazin-2-yl, 2-methylpyrazin-5-yl, pyridazin-3-yl, pyrimidin-4-yl, 1-methylpyrrol-2-yl and thien-3-yl;

$R^2$ represents methyl, ethyl and propyl;

$R^3$ represents hydrogen, chloro or bromo; and $R^4$ represents 5-methylpyrazol-3-yl, 5-ethylpyrazol-3-yl, 5-isopropylpyrazol-3-yl, 5-propylpyrazol-3-yl, 5-t-butylpyrazol-3-yl and 5-cyclopropylpyrazol-3-yl;

or a pharmaceutically acceptable salt or solvate thereof.

Examples of compounds of the invention include:

5-Bromo-2-(3-methylisoxazol-5-ylmethylamino)-4-(5-methyl-1H-pyrazol-3-ylamino)pyrimidine, 5-Chloro-2-(3-methylisoxazol-5-ylmethylamino)-4-(5-methyl-1H-pyrazol-3-ylamino)pyrimidine, 5-Bromo-2-(3-methylisoxazol-5-ylmethylamino)-4-(5-cyclopropyl-1H-pyrazol-3-ylamino)pyrimidine, 5-Chloro-2-(3-isopropylisoxazol-5-ylmethylamino)-4-(5-methyl-1H-pyrazol-3-ylamino)pyrimidine, 5-Chloro-2-(3-phenylisoxazol-5-ylmethylamino)-4-(5-methyl-1H-pyrazol-3-ylamino)pyrimidine, 5-Bromo-2-[3-(2-methoxyphenyl)isoxazol-5-ylmethylamino]-4-(5-methyl-1H-pyrazol-3-ylamino)pyrimidine, 5-Chloro-2-[3-(2-methoxyphenyl)isoxazol-5-ylmethylamino]-4-(5-methyl-1H-pyrazol-3-ylamino)pyrimidine, 5-Chloro-2-(3-pyrid-2-ylisoxazol-5-ylmethylamino)-4-(5-methyl-1H-pyrazol-3-ylamino)pyrimidine, 5-Bromo-2-(3-pyrid-2-ylisoxazol-5-ylmethylamino)-4-(5-methyl-1H-pyrazol-3-ylamino)pyrimidine, 5-Bromo-2-(3-methylisoxazol-5-ylmethylamino)-4-(5-tert-butyl-1H-pyrazol-3-ylamino)pyrimidine, 5-Chloro-2-(3-methylisoxazol-5-ylmethylamino)-4-(5-tert-butyl-1H-pyrazol-3-ylamino)pyrimidine, 5-Bromo-2-(3-methylisoxazol-5-ylmethylamino)-4-(5-ethyl-1H-pyrazol-3-ylamino)pyrimidine, 5-Bromo-2-(2-fur-2-ylethylamino)-4-(5-methyl-1H-pyrazol-3-ylamino)pyrimidine, 5-Bromo-2-(pyrid-3-ylmethylamino)-4-(5-tert-butyl-1H-pyrazol-3-ylamino)pyrimidine, 5-Chloro-2-(pyrid-3-ylmethylamino)-4-(5-tert-butyl-1H-pyrazol-3-ylamino)pyrimidine, 5-Chloro-2-(pyrid-2-ylmethylamino)-4-(5-tert-butyl-1H-pyrazol-3-ylamino)pyrimidine, 5-Bromo-2-(pyrid-3-ylmethylamino)-4-(5-methyl-1H-pyrazol-3-ylamino)pyrimidine, 5-Bromo-2-[2-(imidazol-4-ylethyl)amino]-4-(5-methyl-1H-pyrazol-3-ylamino)pyrimidine, 5-Bromo-2-(pyrid-2-ylmethylamino)-4-(5-methyl-1H-pyrazol-3-ylamino)pyrimidine, 5-Chloro-2-[2-(pyrid-2-yl)ethylamino]-4-(5-methyl-1H-pyrazol-3-ylamino)pyrimidine, 5-Bromo-2-[2-(pyrid-3-yl)ethylamino]-4-(5-methyl-1H-pyrazol-3-yamino)pyrimidine, 5-Bromo-2-(5-methylpyrazin-2-ylmethylamino)-4-(5-methyl-1H-pyrazol-3-ylamino)pyrimidine, 5-Bromo-2-(pyrid-3-ylmethylamino)-4-(5-cyclopropyl-1H-pyrazol-3-ylamino)pyrimidine, and pharmaceutically acceptable salts and solvates of any one thereof.

In a further aspect of the invention, particular compounds of the invention are any one of Examples 3, 5, 8, 9, 11, 12, 34, 39, 40, 41, 47, 48, 68, 70 and 79 or pharmaceutically acceptable salts and solvates of any one thereof.

In another aspect of the invention, particular compounds of the invention are any one of the Examples or pharmaceutically acceptable salts and solvates of any one thereof.

The present invention further provides a process for the preparation of a compound of formula (I) as defined above, or a pharmaceutically acceptable salt or solvate thereof, which comprises:

(i) reacting a compound of formula

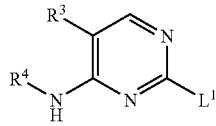

(II)

wherein L¹ represents a leaving group (e.g. halogen or sulphonyloxy such as methanesulphonyloxy or toluene-4-sulphonyloxy) and $R^3$ and $R^4$ are as defined in formula (I), with a compound of formula (III), $H_2N—R^2—R^1$, wherein $R^1$ and $R^2$ are as defined in formula (I); or (ii) reacting a compound of formula

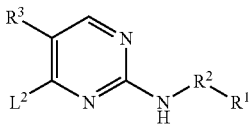

(IV)

wherein L² represents a leaving group (e.g. halogen or sulphonyloxy such as methanesulphonyloxy or toluene-4-sulphonyloxy) and $R^1$, $R^2$ and $R^3$ are as defined in formula (I), with a compound of formula (V), $H_2N—R^4$, wherein $R^4$ is as defined in formula (I); or (iii) reacting a compound of formula

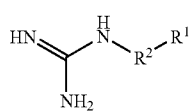

(VI)

wherein $R^1$ and $R^2$ are as defined in formula (I), with a compound of formula

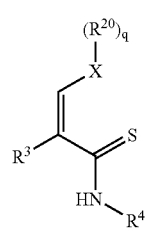

(VII)

wherein X represents an oxygen atom and q is 1 or X represents a nitrogen atom and q is 2, each $R^{20}$ independently represents a $C_1$-$C_6$alkyl group and $R^3$ and $R^4$ are as defined in formula (I); or (iv) when $R^4$ represents a substituted pyrazolyl, reacting a compound of formula

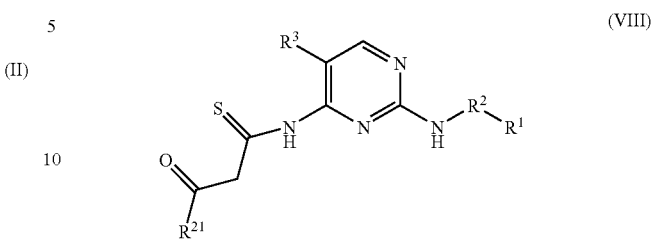

(VIII)

wherein $R^{21}$ represents a $C_1$-$C_6$alkyl or $C_3$-$C_6$cycloalkyl group and $R^1$, $R^2$ and $R^3$ are as defined in formula (I) with hydrazine;

and optionally after (i), (ii), (iii) or (iv) carrying out one or more of the following:
  converting the compound obtained to a further compound of the invention
  forming a pharmaceutically acceptable salt or solvate of the compound.

Processes (i) and (ii) may conveniently be carried out as follows:
a) in the presence of a suitable solvent for example a ketone such as acetone or an alcohol such as ethanol or butanol or an aromatic hydrocarbon such as toluene or N-methylpyrrolid-2-one, optionally in the presence of a suitable acid for example an inorganic acid such as hydrochloric acid or sulphuric acid, or an organic acid such as acetic acid or formic acid (or a suitable Lewis acid) and at a temperature in the range from 0° C. to reflux, particularly reflux; or
b) under standard Buchwald conditions (for example see *J. Am. Chem. Soc.*, 118, 7215; *J. Am. Chem. Soc.*, 119, 8451; *J. Org. Chem.*, 62, 1568 and 6066) for example in the presence of palladium acetate, in a suitable solvent for example an aromatic solvent such as toluene, benzene or xylene, with a suitable base for example an inorganic base such as caesium carbonate or an organic base such as potassium-t-butoxide, in the presence of a suitable ligand such as 2,2'-bis(diphenylphosphino)-1,1'-binaphthyl and at a temperature in the range from 25 to 80° C.

Process (iii) may conveniently be carried out in a suitable solvent such as N-methylpyrrolidinone or butanol at a temperature in the range from 100-200° C., in particular in the range from 150-170° C. The reaction is preferably conducted in the presence of a suitable base such as, for example, sodium methoxide or potassium carbonate.

Process (iv) may be carried out in a suitable solvent, for example, an alcohol such as ethanol or butanol at a temperature in the range from 50-120° C., in particular in the range from 70-100° C.

Compounds of formulae (II), (III), (IV), (V), (VI), (VII) and (VIII) are either commercially available, are known in the literature or may be prepared using known techniques.

Compounds of formula (I) can be converted into further compounds of formula (I) using standard procedures. Examples of the types of conversion reactions that may be used include introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid; the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of reduction reactions include the reduction of a nitro group to an amino group by catalytic hydrogenation with a nickel catalyst or by treatment with iron in the presence of hydrochloric acid with heating; and particular examples of oxidation reactions include oxidation of alkylthio to alkylsulphinyl or alkylsulphonyl.

It will be appreciated by those skilled in the art that in the processes of the present invention certain functional groups such as hydroxyl or amino groups in the starting reagents or intermediate compounds may need to be protected by protecting groups. Thus, the preparation of the compounds of formula (I) may involve, at various stages, the addition and removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', 2nd edition, T. W. Greene and P. G. M. Wuts, Wiley-Interscience (1991).

The compounds of formula (I) above may be converted to a pharmaceutically acceptable salt or solvate thereof, preferably an acid addition salt such as a hydrochloride, hydrobromide, phosphate, acetate, fumarate, maleate, tartrate, citrate, oxalate, methanesulphonate or p-toluenesulphonate, or an alkali metal salt such as a sodium or potassium salt.

Certain compounds of formula (I) are capable of existing in stereoisomeric forms. It will be understood that the invention encompasses the use of all geometric and optical isomers (including atropisomers) of the compounds of formula (I) and mixtures thereof including racemates. The use of tautomers and mixtures thereof also form an aspect of the present invention. For example where $R^4$ is pyrazolyl; pyrazolyl-5-yl and pyrazolyl-3-yl are tautomers of the same compound.

The compounds of formula (I) have activity as pharmaceuticals, in particular as modulators or inhibitors of insulin-like growth factor-1 receptor (IGF-1R) activity, and may be used in the treatment of proliferative and hyperproliferative diseases/conditions, examples of which include the following cancers:

(1) carcinoma, including that of the bladder, brain, breast, colon, kidney, liver, lung, ovary, pancreas, prostate, stomach, cervix, thyroid and skin;
(2) hematopoietic tumors of lymphoid lineage, including acute lymphocytic leukaemia, B-cell lymphoma and Burketts lymphoma;
(3) hematopoietic tumours of myeloid lineage, including acute and chronic myelogenous leukaemias and promyelocytic leukaemia;
(4) tumours of mesenchymal origin, including fibrosarcoma and rhabdomyosarcoma; and
(5) other tumours, including melanoma, seminoma, tetratocarcinoma, neuroblastoma and glioma.

The compounds of the invention are especially useful in the treatment of tumors of the breast and prostate.

Thus, the present invention provides a compound of formula (I), or a pharmaceutically-acceptable salt or solvate thereof, as hereinbefore defined for use in therapy.

In a further aspect, the present invention provides the use of a compound of formula (I), or a pharmaceutically acceptable salt or solvate thereof, as hereinbefore defined in the manufacture of a medicament for use in therapy.

In the context of the present specification, the term "therapy" also includes "prophylaxis" unless there are specific indications to the contrary. The terms "therapeutic" and "therapeutically" should be construed accordingly.

The invention also provides a method of treating cancer which comprises administering to a patient in need thereof a therapeutically effective amount of a compound of formula (I), or a pharmaceutically acceptable salt or solvate thereof, as hereinbefore defined.

The invention still further provides a method of modulating insulin-like growth factor-1 receptor (IGF-1R) activity which comprises administering to a patient in need thereof a therapeutically effective amount of a compound of formula (I), or a pharmaceutically acceptable salt or solvate thereof, as hereinbefore defined.

The compounds of formula (I) and pharmaceutically acceptable salts and solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I), or a pharmaceutically acceptable salt or solvate thereof, as hereinbefore defined, in association with a pharmaceutically acceptable adjuvant, diluent or carrier.

The invention further provides a process for the preparation of a pharmaceutical composition of the invention which comprises mixing a compound of formula (I), or a pharmaceutically acceptable salt or solvate thereof, as hereinbefore defined, with a pharmaceutically acceptable adjuvant, diluent or carrier.

The pharmaceutical compositions may be administered topically (e.g. to the skin or to the lung and/or airways) in the form, e.g., of creams, solutions, suspensions, heptafluoroalkane aerosols and dry powder formulations; or systemically, e.g. by oral administration in the form of tablets, capsules, syrups, powders or granules; or by parenteral administration in the form of solutions or suspensions; or by subcutaneous administration; or by rectal administration in the form of suppositories; or transdermally.

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedure well known in the art.

Compositions for administration by insufflation may be in the form of a finely divided powder containing particles of average diameter of, for example, 30μ or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The size of the dose for therapeutic purposes of a compound of the invention will naturally vary according to the nature and severity of the conditions, the age and sex of the animal or patient and the route of administration, according to well known principles of medicine.

In general, a compound of the invention will be administered so that a daily dose in the range, for example, from 0.5 mg to 75 mg active ingredient per kg body weight is received, given if required in divided doses. In general lower doses will be administered when a parenteral route is employed. Thus, for example, for intravenous administration, a dose in the range, for example, from 0.5 mg to 30 mg active ingredient per kg body weight will generally be used. Similarly, for administration by inhalation, a dose in the range, for example, from 0.5 mg to 25 mg active ingredient per kg body weight will generally be used. Oral administration is however preferred. For example, a formulation intended for oral administration to humans will generally contain, for example, from 0.5 mg to 2 g of active ingredient.

For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

EXAMPLES

The invention will now be further described with reference to the following illustrative examples in which, unless stated otherwise:
(i) temperatures are given in degrees Celsius (° C.); operations were carried out at room or ambient temperature, that is, at a temperature in the range of 18-25° C.;
(ii) organic solutions were dried over anhydrous magnesium sulphate; evaporation of solvent was carried out using a rotary evaporator under reduced pressure (600-4000 Pascals; 4.5-30 mmHg) with a bath temperature of up to 60° C.;
(iii) chromatography means flash chromatography on silica gel; thin layer chromatography (TLC) was carried out on silica gel plates;
(iv) in general, the course of reactions was followed by TLC and reaction times are given for illustration only;
(v) final products had satisfactory proton nuclear magnetic resonance (NMR) spectra and/or mass spectral data;
(vi) yields are given for illustration only and are not necessarily those which can be obtained by diligent process development; preparations were repeated if more material was required;
(vii) when given, NMR data is in the form of delta values for major diagnostic protons, given in parts per million (ppm) relative to tetramethylsilane (TMS) as an internal standard, determined at 300 MHz, in DMSO-$d_6$+$CD_3COOD$ unless otherwise indicated;
(viii) chemical symbols have their usual meanings; SI units and symbols are used;
(ix) solvent ratios are given in volume:volume (v/v) terms; and
(x) mass spectra were run with an electron energy of 70 electron volts in the chemical ionization (CI) mode using a direct exposure probe; where indicated ionization was effected by electron impact (EI), fast atom bombardment (FAB) or electrospray (ESP); values for m/z are given; generally, only ions which indicate the parent mass are reported; and unless otherwise stated, the mass ion quoted is $(MH)^+$;
(xi) the following abbreviations have been used:
THF tetrahydrofuran;
DMF N,N-dimethylformamide;
EtOAc ethyl acetate;
DCM dichloromethane; and
DMSO dimethylsulphoxide.

Example 1

5-Bromo-2-(3-methylisoxazol-5-ylmethylamino)-4-(5-methyl-1H-pyrazol-3-ylamino) pyrimidine A mixture of 5-aminomethyl-3-methylisoxazole hydrochloride (890 mg, 6.0 mmol), 5-bromo-2-chloro-4-(5-methyl-1H-pyrazol-3-ylamino)pyrimidine (Method 1; 578 mg, 2.0 mmol) and N,N-diisopropylethylamine (1.4 ml, 8.0 mmol) in 1-butanol (10 ml) was heated at 120° C. for 18 hours. The mixture was allowed to cool to ambient temperature and volatiles removed by evaporation. The residue was triturated with ether and the product collected by filtration to give the titled compound (225 mg, 31%). $^1$H NMR (DMSO): δ 2.15 (s, 3H), 2.2 (s, 3H), 4.5 (m, 2H), 6.1 (br s, 2H), 7.6 (br s, 1H), 8.0 (br s, 2H), 12.05 (br s, 1H); MS: m/z 366.

Examples 2-12

Following a similar procedure to Example 1, the following compounds were synthesised after replacement with a suitable pyrimidine (SM1) and amine (SM2) (the NMR was recorded in DMSO-d6). Where a starting material is not indicated, this compound is commercially available.

| Ex | Compound | NMR | m/z | SM1 | SM2 |
|---|---|---|---|---|---|
| 2[1] | 5-Chloro-2-(3-methylisoxazol-5-ylmethylamino)-4-(5-methyl-1H-pyrazol-3-ylamino)pyrimidine | 2.15(s, 3H), 2.20(s, 3H), 4.45(d, 2H), 6.2-6.0(m, 2H), 7.6(br s, 1H), 7.95(s, 1H), 8.5(br s, 1H), 12.04(br s, 1H) | 320 | Meth 10 | |
| 3[1,2] | 5-Bromo-2-(3-methylisoxazol-5-ylmethylamino)-4-(5-cyclopropyl-1H-pyrazol-3-ylamino)pyrimidine | 0.6(br s, 2H), 0.9(m, 2H), 1.8(m, 1H), 2.15(s, 3H), 4.5(m, 2H), 6.0-6.2(br s, 2H), 8.05(s, 1H) | 390 | Meth 11 | |
| 4[1] | 5-Chloro-2-(3-isopropylisoxazol-5-ylmethylamino)-4-(5-methyl-1H-pyrazol-3-ylamino)pyrimidine | 1.2(d, 6H), 2.2(s, 3H), 2.9(m, 1H), 4.5(m, 2H), 6.2(br s, 2H), 7.6(br s, 1H), 7.98(s, 1H), 12.04(br s, 1H) | 348 | Meth 10 | Meth 57 |
| 5[1,2] | 5-Chloro-2-(3-phenylisoxazol-5-ylmethylamino)-4-(5-methyl-1H-pyrazol-3-ylamino)pyrimidine | 2.2(s, 3H), 4.6(m, 2H), 6.78(s, 1H), 7.4(m, 3H), 7.6(br s, 1H), 7.8(m, 2H), 8.0(s, 1H), 8.45(s, 1H), 12.0(br s, 1H) | 382 | Meth 10 | Meth 56 |
| 6[1,2] | 5-Bromo-2-[3-(2-methoxyphenyl)isoxazol-5-ylmethylamino]-4-(5-methyl-1H-pyrazol-3-ylamino)pyrimidine | 2.2(s, 3H), 3.8(s, 3H), 4.6(m, 2H), 6.0-6.2(m, 1H), 6.6(s, 1H), 7.0(t, 1H), 7.1(d, 1H), 7.45(m, 1H), 7.7(s, 2H), 8.1(s, 2H), 12.1(br s, 1H) | 456 | Meth 1 | Meth 58 |
| 7[1,2] | 5-Chloro-2-[3-(2-methoxyphenyl)isoxazol-5-ylmethylamino]-4-(5-methyl- | 2.2(s, 3H), 3.8(s, 3H), 4.5-4.7(m, 2H), 6.0-6.4(br s, 1H), 6.6(s, 1H), 7.0(t, 1H), | 412 | Meth 10 | Meth 58 |

-continued

| Ex | Compound | NMR | m/z | SM1 | SM2 |
|---|---|---|---|---|---|
|  | 1H-pyrazol-3-ylamino)pyrimidine | 7.15(d, 1H), 7.45(m, 1H), 7.55-7.7(m, 2H), 8.0(s, 1H), 8.5(br s, 1H), 12.05(s, 1H) |  |  |  |
| 8 | 5-Chloro-2-(3-pyrid-2-ylisoxazol-5-ylmethylamino)-4-(5-methyl-1H-pyrazol-3-ylamino)pyrimidine | 2.2(s, 3H), 4.6(m, 2H), 6.7(s, 1H), 7.43(m, 1H), 7.63(br s, 1H), 7.9-8.0(m, 3H), 8.48(s, 1H), 8.65(d, 1H), 12.02(br s, 1H) | 383 | Meth 10 | Meth 70 |
| 9[1] | 5-Bromo-2-(3-pyrid-2-ylisoxazol-5-ylmethylamino)-4-(5-methyl-1H-pyrazol-3-ylamino)pyrimidine | 2.2(s, 3H), 4.6(m, 2H), 6.0-6.6(m, 1H), 6.7(s, 1H), 7.5(m, 1H), 7.7(br s, 1H), 7.9-8.2(m, 4H), 8.7(d, 1H), 12.1(br s, 1H) | 427 | Meth 1 | Meth 70 |
| 10[1,2] | 5-Bromo-2-(3-methylisoxazol-5-ylmethylamino)-4-(5-tert-butyl-1H-pyrazol-3-ylamino)pyrimidine | 1.25(s, 9H), 2.05(s, 3H), 4.50(d, 2H), 6.05(s, 1H), 7.60(s, 1H), 8.05(s, 1H), 12.07(s, 1H) | 406 | Meth 12 |  |
| 11[1,2] | 5-Chloro-2-(3-methylisoxazol-5-ylmethylamino)-4-(5-tert-butyl-1H-pyrazol-3-ylamino)pyrimidine | 1.23(s, 9H), 2.13(s, 3H), 4.50(d, 2H), 6.03(br s, 1H), 6.32(br s, 1H,), 7.55(br s, 1H), 7.95(s, 1H), 12.05(br s, 1H) | 362 | Meth 13 |  |
| 12[2] | 5-Bromo-2-(3-methylisoxazol-5-ylmethylamino)-4-(5-ethyl-1H-pyrazol-3-ylamino)pyrimidine | 1.16(t, 3H), 2.13(s, 3H), 2.53(q, 2H), 4.47(d, 2H), 6.05(s, 1H), 7.58(s, 1H), 8.03(br s, 2H), 12.06(s, 1H) | 378 | Meth 14 |  |

[1]Required aqueous work-up.
[2]Purified by column chromatography on silica gel eluting with DCM/methanol (95:5).

Example 13

5-Bromo-2-(2-fur-2-ylethylamino)-4-(5-methyl-1H-pyrazol-3-ylamino)pyrimidine

A mixture of 5-bromo-2-chloro-4-(5-methyl-1H-pyrazol-3-ylamino)pyrimidine (Method 1; 290 mg, 11.0 mmol), 2-(2-aminoethyl)furan (330 mg, 3.0 mmol) and 1-butanol (5 ml) was heated at 120° C. for 5 hours. The mixture was allowed to cool to ambient temperature and the volatiles removed by evaporation. The residue was dissolved in DCM and washed with water followed by brine. The organics were separated, dried (MgSO$_4$) and the solvent removed by evaporation. The residue was triturated with ether, the solid product collected and purified by column chromatography on silica gel eluting with DCM/methanol (95:5) to give the titled compound (80 mg, 22%). $^1$H NMR (DMSO): δ 2.1 (s, 3H), 2.85 (m, 2H), 3.45 (m 2H), 6.10 (m, 1H), 6.35 (m, 1H), 6.4 (br s, 1H), 7.15 (br s, 1H), 7.5 (s, 1H), 8.0 (br s, 2H), 12.05 (br s, 1H); MS: m/z 363.

Examples 14-106

Following a similar procedure to Example 13, the following compounds were synthesised after replacement with appropriate pyrimidine (SM1) and amine (SM2) starting materials. Where a starting material is not indicated, this compound is commercially available.

| Ex | Compound | NMR | m/z | SM1 | SM2 |
|---|---|---|---|---|---|
| 14[1,7] | 5-Bromo-2-(pyrid-3-ylmethylamino)-4-(5-tert-butyl-1H-pyrazol-3-ylamino)pyrimidine | 1.20(s, 9H), 4.50(d, 2H), 6.05(s, 1H), 7.30(m, 1H), 7.60(m, 3H), 8.00(s, 2H), 8.40(d, 1H), 8.45(s, 1H), 12.07(s, 1H) | 402 | Meth 12 |  |
| 15[2,7] | 5-Chloro-2-(pyrid-3-ylmethylamino)-4-(5-tert-butyl-1H-pyrazol-3-ylamino)pyrimidine | 1.19(s, 9H), 4.47(d, 2H), 7.28(t, 1H) | 358 | Meth 13 |  |
| 16[2,7] | 5-Chloro-2-(pyrid-2-ylmethylamino)-4-(5-tert-butyl-1H-pyrazol-3-ylamino)pyrimidine | 1.14(s, 9H), 4.56(d, 2H), 6.17(br s, 1H), 7.61(s, 1H), 7.69(t, 1H), 7.94(s, 1H), 8.39(s, 1H), 8.46(d, 1H), 12.01(s, 1H) | 358 | Meth 13 |  |
| 17[3,7] | 5-Bromo-2-(pyrid-3-ylmethylamino)-4-(5-methyl-1H-pyrazol-3-ylamino)pyrimidine | 2.17(s, 3H), 4.42(d, 2H), 7.28(m, 1H), 7.6(m, 2H), 8.0(br s, 2H), 8.4(d, 1H), 8.5(s, 1H), 12.01(br s, 1H) | 360 | Meth 1 |  |
| 18[3,7] | 5-Bromo-2-[2-(imidazol-4-ylethyl)amino]-4-(5-methyl-1H-pyrazol-3-ylamino)pyrimidine | 2.2(s, 3H), 2.75(t, 2H), 3.45(m, 2H), 6.4(br s, 1H), 6.85(s, 1H), 7.15(br s, 1H), 7.5(s, 1H), 8.0(br s, 1H) | 363 | Meth 1 |  |

-continued

| Ex | Compound | NMR | m/z | SM1 | SM2 |
|---|---|---|---|---|---|
| 19[4,5,7] | 5-Bromo-2-(pyrid-2-ylmethylamino)-4-(5-methyl-1H-pyrazol-3-ylamino)pyrimidine | 2.1(br s, 3H), 4.5(d, 2H), 7.2(m, 2H), 7.6(br s, 1H), 7.7(m, 1H), 7.9(s, 1H), 8.0(s, 1H), 8.5(d, 1H), 11.97(br s, 1H) | 360 | Meth 1 | |
| 20[7] | 5-Chloro-2-[2-(pyrid-2-yl)ethylamino]-4-(5-methyl-1H-pyrazol-3-ylamino)pyrimidine | 2.15(s, 3H), 2.95(m, 2H), 3.6(m, 2H), 6.5(s, 1H), 7.05(br s, 1H), 7.2(m, 2H), 7.65(t, 1H), 7.9(s, 1H), 8.3(br s, 1H), 8.5(m, 1H), 12.02(br s, 1H) | 330 | Meth 10 | |
| 21[4,5,7] | 5-Bromo-2-[2-(pyrid-3-yl)ethylamino]-4-(5-methyl-1H-pyrazol-3-ylamino)pyrimidine | 2.1(br s, 3H), 2.9(t, 2H), 3.5(t, 2H), 6.4(s, 1H), 6.95(t, 1H), 7.05(t, 1H), 7.1(s, 1H), 7.3(d, 1H), 7.5(m, 1H), 8.0(s, 1H) | 374 | Meth 1 | |
| 22[4,5,6,7] | 5-Bromo-2-(5-methylpyrazin-2-ylmethylamino)-4-(5-methyl-1H-pyrazol-3-ylamino)pyrimidine | 2.2(s, 3H), 2.45(s, 3H), 4.6(d, 2H), 6.2(s, 1H), 7.15(br s, 1H), 8.0(s, 1H), 8.4(s, 1H), 8.43(s, 1H) | 375 | Meth 1 | |
| 23[7] | 5-Bromo-2-(pyrid-3-ylmethylamino)-4-(5-cyclopropyl-1H-pyrazol-3-ylamino)pyrimidine | 0.4-0.9(m, 4H), 1.8(br s, 1H), 4.4(m, 2H), 5.8-6.5(m, 1H), 7.3(m, 1H), 7.6(br s, 2H), 8.0(s, 2H), 8.4(m, 1H), 8.5(s, 1H), 12.1-12.3(m, 1H) | 386 | Meth 11 | |
| 24 | 5-Bromo-2-[3-(2-chlorophenyl)isoxazol-5-ylmethylamino]-4-(5-methyl-1H-pyrazol-3-ylamino)pyrimidine | 2.19(s, 3H), 4.64(s, 2H), 5.74(s, 1H), 6.18(br s, 1H), 6.64(s, 1H), 7.41-7.55(m, 2H), 7.74(t, 1H), 8.07(s, 1H) | 460 | Meth 1 | Meth 59 |
| 25 | 5-Bromo-2-[3-(2-chlorophenyl)isoxazol-5-ylmethylamino]-4-(5-tert-butyl-1H-pyrazol-3-ylamino)pyrimidine | 1.21(s, 9H), 4.67(s, 2H), 6.31(br s, 1H), 6.60(br s, 1H), 7.39-7.54(m, 2H), 7.56-7.66(m, 2H), 8.07(s, 1H) | 502 | Meth 12 | Meth 59 |
| 26 | 4-(5-Methyl-1H-pyrazol-3-ylamino)-2-(pyrid-3-ylmethylamino)pyrimidine | 2.12(s, 3H), 4.46(s, 2H), 6.05(br s, 1H), 6.21(br s, 1H), 7.26-7.35(m, 2H), 7.70(d, 1H), 7.79(d, 1H), 8.39(s, 1H), 8.55(s, 1H) | 282 | Meth 15 | |
| 27 | 5-Bromo-2-[2-(3-methylisoxazol-5-yl)ethylamino]-4-(5-methyl-1H-pyrazol-3-ylamino)pyrimidine | 2.18(s, 6H), 2.96(t, 2H), 3.51(t, 2H), 6.12(s, 1H), 6.36(s, 1H), 8.02(s, 1H) | 378 | Meth 1 | Meth 83 |
| 28 | 5-Chloro-2-[3-(2-chlorophenyl)isoxazol-5-ylmethylamino]-4-(5-tert-butyl-1H-pyrazol-3-ylamino)pyrimidine | 1.21(s, 9H), 4.65(s, 2H), 6.31(br s, 1H), 6.60(br s, 1H), 7.39-7.52(m, 2H), 7.57-7.65(m, 2H), 7.99(s, 1H) | 458 | Meth 13 | Meth 59 |
| 29 | 5-Chloro-4-(5-propyl-1H-pyrazol-3-ylamino)-2-(pyrid-2-ylmethylamino)pyrimidine | 0.88(t, 3H), 1.50(br s, 2H), 2.44(br s, 2H), 4.53(s, 2H), 5.87(br s, 1H), 7.16-7.29(m, 2H), 7.70(t, H), 7.94(s, 1H), 8.48(d, 1H) | 344 | Meth 16 | |
| 30 | 5-Bromo-4-(5-cyclopropyl-1H-pyrazol-3-ylamino)-2-(pyrid-2-ylmethylamino)pyrimidine | 0.60(br s, 2H), 0.89(d, 2H), 1.78(br s, 1H), 4.51(s, 2H), 5.87(br s, 1H), 7.16-7.31(m, 2H), 7.69(t, 1H), 8.01(s, 1H), 8.49(d, 1H) | 386 | Meth 11 | |
| 31 | 5-Chloro-4-(5-ethyl-1H-pyrazol-3-ylamino)-2-(pyrid-2-ylmethylamino)pyrimidine | 1.10(br s, 3H), 2.44(br s, 2H), 4.49(s, 2H), 6.01(br s, 1H), 7.17-7.29(m, 2H), 7.70(t, 1H), 7.93(s, 1H), 8.49(d, 1H) | 330 | Meth 17 | |
| 32 | 5-Bromo-4-(5-ethyl-1H-pyrazol-3-ylamino)-2-(pyrid-2-ylmethylamino)pyrimidine | 1.10(br s, 3H), 2.54(br s, 2H), 4.54(s, 2H), 6.00(br s, 1H), 7.17-7.30(m, 2H), 7.69(t, 1H), 7.99(s, 1H), 8.49(d, 1H) | 374 | Meth 14 | |
| 33[7] | 5-Bromo-4-(5-propyl-1H-pyrazol-3-ylamino)-2-(pyrid-2-ylmethylamino)pyrimidine | 0.88(br s, 3H), 1.51(br s, 2H), 2.45(br s, 2H), 4.55(s, 2H), 5.98(br s, 1H), 7.15-7.30(m, 2H), 7.59(s, 1H), 7.72(t, 1H), 7.95(s, 1H), 8.01(s, 1H), 8.50(d, 1H), 11.98(s, 1H) | 388 | Meth 18 | |
| 34[7] | 5-Chloro-2-[3-(2-fluorophenyl)isoxazol-5-ylmethylamino]-4-(5-methyl-1H-pyrazol-3-ylamino)pyrimidine | 2.19(s, 3H), 4.61(s, 2H), 6.21(br s, 1H), 6.66(s, 1H), 7.27-7.40(m, 2H), 7.50-7.60(m, 1H), 7.66(br s, 1H), 7.86(t, 1H), 7.99(s, 1H), 8.50(br s, 1H), 12.04(s, 1H) | 400 | Meth 10 | Meth 60 |

-continued

| Ex | Compound | NMR | m/z | SM1 | SM2 |
|---|---|---|---|---|---|
| 35 | 5-Chloro-4-(5-isopropyl-1H-pyrazol-3-ylamino)-2-(pyrid-2-ylmethylamino)pyrimidine | 1.15(br s, 6H), 2.81(br s, 1H), 4.55(s, 2H), 6.20(br s, 1H), 7.15-7.32(m, 2H), 7.71(t, 1H), 7.95(s, 1H), 8.46(d, 1H) | 344 | Meth 19 | |
| 36[7] | 5-Bromo-4-(5-tert-butyl-1H-pyrazol-3-ylamino)-2-[3-(2-trifluoromethoxyphenyl)isoxazol-5-ylmethylamino]pyrimidine | 1.26(s, 9H), 4.65(s, 2H), 6.28(br s, 1H), 6.56(br s, 1H), 7.46-7.56(m, 2H), 7.62-7.66(m, 1H), 7.72(br s, 1H), 7.85(d, 1H), 8.05(s, 1H), 12.06(s, 1H) | 552 | Meth 12 | Meth 61 |
| 37 | 5-Chloro-4-(5-cyclopropyl-1H-pyrazol-3-ylamino)-2-(pyrid-2-ylmethylamino)pyrimidine | 0.60(br s, 2H), 0.88(d, 2H), 1.78(br s, 1H), 4.52(s, 2H), 5.95(br s, 1H), 7.16-7.31(m, 2H), 7.69(t, 1H), 7.91(s, 1H), 8.50(d, 1H) | 342 | Meth 20 | |
| 38[8] | 5-Chloro-2-[3-(2-cyanophenyl)isoxazol-5-ylmethylamino]-4-(5-methyl-1H-pyrazol-3-ylamino)pyrimidine | 2.18(s, 3H), 4.68(s, 2H), 6.27(s, 1H), 6.77(s, 1H), 7.64(dt, 1H), 7.77(dt, 1H), 7.84(dd, 1H), 7.90(dd, 1H), 7.96(s, 1H) | 407 | Meth 10 | Meth 81 |
| 39 | 5-Bromo-2-[3-(2-fluorophenyl)isoxazol-5-ylmethylamino]-4-(5-methyl-1H-pyrazol-3-ylamino)pyrimidine | 2.19(s, 3H), 4.63(s, 2H), 6.27(br s, 1H), 6.66(s, 1H), 7.30-7.44(m, 2H), 7.50-7.61(m, 1H), 7.87(t, 1H), 8.09(s, 1H) | 444 | Meth 1 | Meth 60 |
| 40[7] | 5-Chloro-2-[3-(2-fluorophenyl)isoxazol-5-ylmethylamino]-4-(5-tert-butyl-1H-pyrazol-3-ylamino)pyrimidine | 1.22(s, 9H), 4.67(s, 2H), 6.38(br s, 1H), 6.64(br s, 1H), 7.28-7.41(m, 2H), 7.50-7.59(m, 1H), 7.69(br s, 1H), 7.85(t, 1H), 8.00(s, 1H), 8.54(br s, 1H), 12.10(s, 1H) | 442 | Meth 13 | Meth 60 |
| 41 | 5-Bromo-4-(5-isopropyl-1H-pyrazol-3-ylamino)-2-(pyrid-2-ylmethylamino)pyrimidine | 1.01-1.25(m, 6H), 2.84(brs, 1H), 4.56(s, 2H), 6.12(br s, 1H), 7.19-7.34(m, 2H), 7.72(t, 1H), 8.04(s, 1H), 8.49(d, 1H) | 388 | Meth 21 | |
| 42[7] | 5-Bromo-2-[3-(2-fluorophenyl)isoxazol-5-ylmethylamino]-4-(5-tert-butyl-1H-pyrazol-3-ylamino)pyrimidine | 1.22(s, 9H), 4.66(s, 2H), 6.34(br s, 1H), 6.62(br s, 1H), 7.28-7.43(m, 2H), 7.51-7.61(m, 1H), 7.72(br s, 1H), 7.86(t, 1H), 8.01-8.18(br s, 2H), 12.10(s, 1H) | 486 | Meth 12 | Meth 60 |
| 43[8] | 5-Bromo-2-[3-(2-cyanophenyl)isoxazol-5-ylmethylamino]-4-(5-methyl-1H-pyrazol-3-ylamino)pyrimidine | 1.69(s, 3H), 4.20(s, 2H), 5.78(s, 1H), 6.27(s, 1H), 7.15(dt, 1H), 7.28(dt, 1H), 7.35(dd, 1H) 7.41(dd, 1H), 7.55(s, 1H) | 451 | Meth 1 | Meth 81 |
| 44[9] | 5-Bromo-2-[1-(3-methylisoxazol-5-yl)ethylamino]-4-(5-methyl-1H-pyrazol-3-ylamino)pyrimidine | 1.50(s, 3H), 2.18(s, 3H), 2.22(s, 3H), 5.18(q, H), 6.10(s, H), 6.23(br s, H), 7.68(br s, H), 8.09(s, H), 8.53(br s, H) | 378 | Meth 1 | Meth 72 |
| 45[9] | 5-Chloro-2-[1-(3-methylisoxazol-5-yl)ethylamino]-4-(5-methyl-1H-pyrazol-3-ylamino)pyrimidine | 1.50(s, 3H), 2.15(s, 3H), 2.24(s, 3H), 5.18(q, H), 6.10(s, H), 6.21(br s, H), 7.73(br s, H), 8.01(s, H), 8.99(br s, H) | 334 | Meth 10 | Meth 72 |
| 46[7] | 5-Bromo-4-(5-ethyl-1H-pyrazol-3-ylamino)-2-(pyrid-3-ylmethylamino)pyrimidine | 1.10(t, 3H), 2.54(q, 2H), 4.42(d, 2H), 7.26(t, 1H), 7.50-7.68(m, 2H), 7.92-8.05(m, 2H), 8.37(d, 1H), 8.45(s, 1H), 12.04(br s, 1H) | 374 | Meth 14 | |
| 47 | 5-Bromo-2-(3-methylisoxazol-5-ylmethylamino)-4-(5-propyl-1H-pyrazol-3-ylamino)pyrimidine | 0.85(t, 3H), 1.58(m, 2H), 2.10(s, 3H), 2.50(t, 2H), 4.50(s, 2H), 6.05(s, 1H), 8.00(s, 1H) | 392 | Meth 18 | |
| 48 | 5-Bromo-2-(3-methylisoxazol-5-ylmethylamino)-4-(5-isopropyl-1H-pyrazol-3-ylamino)pyrimidine | 1.18(d, 6H), 2.10(s, 3H), 2.85(m, 1H), 4.5(s, 2H), 6.00(s, 1H), 6.30(br s, 1H), 8.00(s, 1H) | 392 | Meth 21 | |
| 49 | 5-Bromo-2-[3-(2-ethoxyphenyl)isoxazol-5-ylmethylamino]-4-(5-tert-butyl-1H-pyrazol-3-ylamino)pyrimidine | 1.25(br s, 12H), 4.04(q, 2H), 4.62(s, 2H), 6.35(br s, 1H), 6.65(s, 1H), 7.00(t, 1H), 7.10(d, 1H), 7.40(t, 1H), 7.70(d, 1H), 8.07(s, 1H) | 512 | Meth 12 | Meth 62 |

| Ex | Compound | NMR | m/z | SM1 | SM2 |
|---|---|---|---|---|---|
| 50 | 5-Bromo-4-(5-tert-butyl-1H-pyrazol-3-ylamino)-2-[3-(2-trifluoromethylphenyl)isoxazol-5-ylmethylamino]pyrimidine | 1.30(s, 9H), 4.75(s, 2H), 6.35(br s, 1H), 6.43(br s, 1H), 7.58(d, 1H), 7.75(m, 2H), 7.87(d, 1H), 8.20(s, 1H) | 536 | Meth 12 | Meth 63 |
| 51 | 5-Bromo-2-[3-(2-methylphenyl)isoxazol-5-ylmethylamino]-4-(5-tert-butyl-1H-pyrazol-3-ylamino)pyrimidine | 1.23(s, 9H), 2.36(s, 3H), 4.65(s, 2H), 6.36(br s, 1H), 6.54(br s, 1H), 7.32(m, 3H), 7.44(d, 1H), 8.20(s, 1H) | 482 | Meth 12 | Meth 64 |
| 52[7] | 5-Bromo-2-[2-(pyridazin-3-yl)ethylamino]-4-(5-tert-butyl-1H-pyrazol-3-ylamino)pyrimidine | 1.19(br s, 9H), 3.19(t, 2H), 3.65(q, 2H), 6.41(br s, 1H), 7.54(m, 2H), 7.98(s, 1H), 9.06(d, 1H) | 417 | Meth 12 | J Am Chem Soc, 1950, 72, 3539 |
| 53 | 5-Bromo-2-[3-(2-bromophenyl)isoxazol-5-ylmethylamino]-4-(5-methyl-1H-pyrazol-3-ylamino)pyrimidine | 2.18(s, 3H), 4.63(s, 2H), 6.3(bd, 1H), 6.62(br s, 1H), 7.49(m, 3H), 7.76(d, 1H), 8.07(s, 1H) | 506 | Meth 1 | Meth 65 |
| 54 | 5-Bromo-2-[2-(pyrimidin-4-yl)ethylamino]-4-(5-tert-butyl-1H-pyrazol-3-ylamino)pyrimidine | 1.19(s, 9H), 2.98(t, 2H), 3.62(q, 2H), 6.36(s, 1H), 7.37(d, 1H), 8.13(s, 1H), 8.62(d, 1H), 9.04(s, 1H) | 417 | Meth 12 | J Am Chem Soc, 1950, 72, 3539 |
| 55[7] | 5-Bromo-2-(pyrazin-2-ylmethylamino)-4-(5-tert-butyl-1H-pyrazol-3-ylamino)pyrimidine | 1.19(s, 9H), 4.57(d, 2H), 6.16(br s, 1H), 8.01(s, 1H), 8.48(s, 1H), 8.52(s, 2H) | 403 | Meth 12 | |
| 56 | 5-Bromo-2-(5-methylisoxazol-3-ylmethylamino)-4-(5-tert-butyl-1H-pyrazol-3-ylamino)pyrimidine | 1.24(s, 9H), 2.38(s, 3H), 4.43(s, 2H), 6.07(s, 1H), 6.41(s, 1H), 8.04(s, 1H) | 406 | Meth 12 | Meth 85 |
| 57[7] | 5-Bromo-2-(pyrid-3-ylmethylamino)-4-(5-propyl-1H-pyrazol-3-ylamino)pyrimidine | 0.86(t, 3H), 1.52(m, 2H), 2.47(m, 2H), 4.45(d, 2H), 6.04(br s, 1H), 7.29(t, 1H), 7.60(bt, 1H), 8.00(s, 1H), 8.39(d, 1H), 8.48(s, 1H) | 388 | Meth 18 | |
| 58 | 5-Bromo-4-(5-isopropyl-1H-pyrazol-3-ylamino)-2-(pyrid-3-ylmethylamino)pyrimidine | 1.14(s, 6H), 2.84(m, 1H), 4.46(s, 2H), 6.18(br s, 1H), 7.28(t, 1H), 7.63(bt, 1H), 8.00(s, 1H), 8.38(d, 1H), 8.47(s, 1H) | 388 | Meth 21 | |
| 59 | 5-Bromo-2-[3-(2-methoxypyrid-3-yl)isoxazol-5-ylmethylamino]-4-(5-methyl-1H-pyrazol-3-ylamino)pyrimidine | 2.19(s, 3H), 3.93(s, 3H), 4.62(s, 2H), 6.30(br s, 1H), 6.70(s, 1H), 7.12(dd, 1H), 8.07(s, 1H), 8.14(dd, 1H), 8.29(dd, 1H) | 457 | Meth 1 | Meth 66 |
| 60[7] | 5-Bromo-2-[3-(3-methylpyrazol-4-yl)propylamino]-4-(5-tert-butyl-1H-pyrazol-3-ylamino)pyrimidine | 1.25(s, 9H), 1.71(m, 2H), 2.06(s, 3H), 2.34(m, 2H), 3.24(m, 2H), 6.47(br s, 1H), 7.05(br s, 1H), 7.30(br s, 1H), 7.97(s, 1H), 12.06(br s, 1H) | 433 | Meth 12 | |
| 61[7] | 5-Bromo-2-[3-(3-methylpyrazol-4-yl)propylamino]-4-(5-methyl-1H-pyrazol-3-ylamino)pyrimidine | 1.70(m, 2H), 2.08(s, 3H), 2.18(s, 3H), 2.36(t, 2H), 3.20(m, 2H), 6.40(br s, 1H), 7.03(br s, 1H), 7.26(s, 1H), 7.97(s, 2H), 12.04(s, 1H) | 391 | Meth 1 | |
| 62 | 5-Chloro-4-(5-methyl-1H-pyrazol-3-ylamino)-2-(pyrid-2-ylmethylamino)pyrimidine | 2.12(s, 3H), 4.5(d, 2H), 7.07-7.36(m, 2H), 7.51(br s, 1H), 7.67(m, 1H), 7.91(s, 1H), 8.34(s, 1H), 8.48(d, 1H), 11.96(br s, 1H) | 316 | Meth 10 | |
| 63 | 5-Chloro-4-(5-methyl-1H-pyrazol-3-ylamino)-2-(pyrid-3-ylmethylamino)pyrimidine | 2.15(s, 3H), 4.43(m, 2H), 7.29(s, 1H), 7.43-7.74(m, 2H), 7.92(br s, 1H), 8.23-8.56(m, 3H), 12.0(br s, 1H) | 316 | Meth 10 | |
| 64 | 5-Bromo-4-(5-methyl-1H-pyrazol-3-ylamino)-2-(pyrid-4- | 2.13(s, 3H), 4.43(d, 2H), 7.24(d, 2H), 7.63(br s, 1H), 7.99(s, 2H), 8.44(d, 2H), 11.99(br s, 1H) | 360 | Meth 1 | |

| Ex | Compound | NMR | m/z | SM1 | SM2 |
|---|---|---|---|---|---|
| | ylmethylamino)pyrimidine | | | | |
| 65 | 5-Chloro-2-[2-(imidazol-5-yl)ethylamino]-4-(5-methyl-1H-pyrazol-3-ylamino)pyrimidine | 2.15(s, 3H), 2.74(m, 2H), 3.43(m, 2H), 6.48(br s, 1H), 6.77(br s, 1H), 7.01(br s, 1H), 7.5(s, 1H), 7.9(br s, 1H), 8.31(br s, 1H), 11.6-12.1(m, 2H) | 319 | Meth 10 | |
| 66 | 5-Chloro-2-[3-(3-methoxyphenyl)isoxazol-5-ylmethylamino]-4-(5-methyl-1H-pyrazol-3-ylamino)pyrimidine | 2.19(s, 3H), 3.81(s, 3H), 4.61(s, 2H), 6.05-6.45(m, 1H), 6.81(s, 1H), 7.03(m, 1H), 7.36-7.40(m, 4H), 7.99(s, 1H) | 412 | Meth 10 | Meth 67 |
| 67 | 5-Chloro-4-(5-methyl-1H-pyrazol-3-ylamino)-2-[3-(pyrid-3-yl)isoxazol-5-ylmethylamino]pyrimidine | 2.16(s, 3H), 4.60(s, 2H), 5.97-6.43(m, 1H), 6.88(br s, 1H), 7.49(m, 1H), 7.96(s, 1H), 8.20(m, 1H), 8.64(m, 1H), 9.0(br s, 1H) | 383 | Meth 10 | Meth 68 |
| 68 | 5-Chloro-2-[3-(pyrid-2-yl)isoxazol-5-ylmethylamino]-4-(5-tert-butyl-1H-pyrazol-3-ylamino)pyrimidine | 1.24(s, 9H), 4.66(s, 2H), 6.34(br s, 1H), 6.73(br s, 1H), 7.48(t, 1H), 7.89-7.99(m, 3H), 8.65(d, 1H) | 425 | Meth 13 | Meth 70 |
| 69 | 5-Bromo-4-(5-propyl-1H-pyrazol-3-ylamino)-2-[3-(pyrid-2-yl)isoxazol-5-ylmethylamino]pyrimidine | 0.85(br s, 3H), 1.55(br s, 2H), 2.5(2H, m), 4.63(s, 2H), 6.05-6.52(m, 1H), 6.74(br s, 1H), 7.47(t, 1H), 7.88-7.99(m, 2H), 8.07(s, 1H), 8.66(d, 1H) | 455 | Meth 18 | Meth 70 |
| 70 | 5-Bromo-2-[3-(pyrid-2-yl)isoxazol-5-ylmethylamino]-4-(5-tert-butyl-1H-pyrazol-3-ylamino)pyrimidine | 1.23(s, 9H), 4.66(s, 2H), 6.34(br s, 1H), 6.73(br s, 1H), 7.48(m, 1H), 7.86-8.02(m, 2H), 8.08(s, 1H), 8.65(d, 1H) | 469 | Meth 12 | Meth 70 |
| 71 | 5-Bromo-4-(5-ethyl-1H-pyrazol-3-ylamino)-2-[3-(pyrid-2-yl)isoxazol-5-ylmethylamino]pyrimidine | 1.15(m, 3H), 2.54(m, 2H), 4.64(s, 2H), 6.05-6.53(br s, 1H), 6.74(br s, 1H), 7.46(m, 1H), 7.84-8.02(m, 2H), 8.07(s, 1H), 8.65(d, 1H) | 441 | Meth 14 | Meth 70 |
| 72 | 5-Bromo-4-(5-isopropyl-1H-pyrazol-3-ylamino)-2-[3-(pyrid-2-yl)isoxazol-5-ylmethylamino]pyrimidine | 1.17(m, 6H), 2.80-2.95(m, 1H), 4.64(br s, 1H), 6.18-6.48(br s, 1H), 6.73(br s, 1H), 7.46(m, 1H), 7.82-8.00(m, 2H), 8.07(s, 1H), 8.64(d, 1H) | 455 | Meth 21 | Meth 70 |
| 73[10] | 5-Bromo-2-(5-methylfur-2-ylmethylamino)-4-(5-tert-butyl-1H-pyrazol-3-ylamino)pyrimidine | 1.24(s, 9H), 2.21(s, 3H), 4.48(s, 2H), 5.97(s, 1H), 6.06(br s, 1H), 6.40(br s, 1H), 8.32(s, 1H) | 405 | Meth 12 | |
| 74[10] | 5-Bromo-2-(fur-3-ylmethylamino)-4-(5-methyl-1H-pyrazol-3-ylamino)pyrimidine | 2.25(s, 3H), 4.37(s, 2H), 6.24(s, 1H), 6.47(s, 1H), 7.52(s, 1H), 7.61(s, 1H), 8.35(s, 1H) | 349 | Meth 1 | |
| 75[10] | 5-Bromo-2-(2-cyanopyrid-5-ylmethylamino)-4-(5-tert-butyl-1H-pyrazol-3-ylamino)pyrimidine | 1.15(s, 9H), 4.62(s, 2H), 6.05(s, 1H), 7.86(m, 1H), 7.93(d, 1H), 8.38(s, 1H), 8.60(s, 1H) | 427 | Meth 12 | WO 02/44145 |
| 76[10] | 5-Bromo-2-(pyrid-2-ylmethylamino)-4-(5-tert-butyl-1H-pyrazol-3-ylamino)pyrimidine | 1.19(s, 9H), 4.87(s, 2H), 6.04(s, 1H), 7.90(m, 2H), 8.46(m, 2H), 8.83(d, 1H) | 402 | Meth 12 | |
| 77[10] | 5-Bromo-2-(fur-3-ylmethylamino)-4-(5-tert-butyl-1H-pyrazol-3-ylamino)pyrimidine | 1.24(s, 9H), 4.40(s, 2H), 6.36(br s, 1H), 6.43(br s, 1H), 7.48(br s, 1H), 7.57(br s, 1H), 8.35(s, 1H) | 391 | Meth 12 | |
| 78[10] | 5-Bromo-2-(2-methoxypyrid-5-ylmethylamino)-4-(5-tert-butyl-1H-pyrazol-3-ylamino)pyrimidine | 1.21(s, 9H), 3.92(s, 3H), 4.72(s, 2H), 6.16(s, 1H), 7.61(m, 1H), 7.83(d, 1H), 8.45(m, 2H) | 432 | Meth 12 | WO 95/18097 |
| 79[10] | 5-Bromo-2-(3-bromopyrid-5-ylmethylamino)-4-(5-tert-butyl-1H-pyrazol-3-ylamino)pyrimidine | 1.17(s, 9H), 4.60(s, 2H), 6.13(s, 1H), 8.10(s, 1H), 8.38(s, 1H), 8.52(s, 1H), 8.70(s, 1H) | 480 | Meth 12 | WO 99/00385 |

-continued

| Ex | Compound | NMR | m/z | SM1 | SM2 |
|---|---|---|---|---|---|
| 80[10] | 5-Bromo-2-(fur-2-ylmethylamino)-4-(5-tert-butyl-1H-pyrazol-3-ylamino)pyrimidine | 1.24(s, 9H), 4.56(s, 2H), 6.21(s, 1H), 6.39(br s, 2H), 7.59(s, 1H), 8.34(s, 1H) | 391 | Meth 12 | |
| 81[10] | 5-Bromo-4-(5-methyl-1H-pyrazol-3-ylamino)-2-[2-(thien-3-yl)ethylamino]pyrimidine | 2.21(s, 3H), 2.88(m, 2H), 3.57(m, 2H), 6.34(s, 1H), 6.97(br s, 1H), 7.20(br s, 1H), 7.49(m, 1H), 8.33(s, 1H) | 379 | Meth 1 | |
| 82[7] | 5-Bromo-2-[2-(1-methylpyrrol-2-yl)ethylamino]-4-(5-methyl-1H-pyrazol-3-ylamino)pyrimidine | 2.10(m, 3H), 2.75(t, 2H), 3.3-3.4(m, 5H), 5.80(s, 1H), 5.87(s, 1H), 6.37(m, 1H), 6.60(s, 1H), 7.16(m, 1H), 8.03(m, 2H) | 376 | Meth 1 | Tetrahedron 1999, 55, 11619-11640 |
| 83 | 5-Bromo-2-(3-phenylisoxazol-5-ylmethylamino)-4-(5-methyl-1H-pyrazol-3-ylamino)pyrimidine | 2.15(s, 3H), 4.6(s, 2H), 6.0-6.5(br s, 1H), 6.75(br s, 1H), 7.44(m, 3H), 7.8(m, 2H), 8.05(s, 1H) | 426 | Meth 1 | Meth 56 |
| 84 | 5-Bromo-2-[4-(pyrid-2-yl)pyrid-2-ylmethylamino]-4-(5-methyl-1H-pyrazol-3-ylamino)pyrimidine | 2.11(s, 3H), 4.61(s, 2H), 6.1(br s, 1H), 7.42(t, 1H), 7.98(m, 4H), 8.00(s, 1H), 8.60(d, 1H), 8.67(d, 1H) | 437 | Meth 1 | Meth 100 |
| 85 | 5-Bromo-2-[5-(pyrid-2-yl)pyrid-3-ylmethylamino]-4-(5-methyl-1H-pyrazol-3-ylamino)pyrimidine | 2.12(s, 3H), 4.54(s, 2H), 6.20(br s, 1H), 7.39(t, 1H), 7.89(m, 2H), 8.02(s, 1H), 8.37(d, 1H), 8.55(s, 1H), 8.69(d, 1H), 9.08(s, 1H) | 437 | Meth 1 | Meth 102 |
| 86 | 5-Chloro-2-[5-(pyrid-2-yl)pyrid-3-ylmethylamino]-4-(5-methyl-1H-pyrazol-3-ylamino)pyrimidine | 2.12(s, 3H), 4.54(s, 2H), 6.20(br s, 1H), 7.89(m, 2H), 7.94(s, 1H), 8.38(s, 1H), 8.56(s, 1H), 8.67(d, 1H), 9.08(s, 1H) | 393 | Meth 10 | Meth 102 |
| 87 | 5-Bromo-2-(6-chloropyrid-2-ylmethylamino)-4-(5-methyl-1H-pyrazol-3-ylamino)pyrimidine | 2.15(s, 3H), 4.48(s, 2H), 5.85(br s, 1H), 7.25(d, 1H), 7.35(d, 1H), 7.75(t, 1H), 8.00(s, 1H) | 394 | Meth 1 | Meth 94 |
| 88 | 5-Bromo-2-(3-methylpyrid-2-ylmethylamino)-4-(5-methyl-1H-pyrazol-3-ylamino)pyrimidine | 2.17(s, 3H), 2.30(s, 3H), 4.55(s, 2H), 6.20(br s, 1H), 7.20(t, 1H), 7.55(d, 1H), 8.03(s, 1H), 8.35(d, 1H) | 374 | Meth 1 | Meth 97 |
| 89 | 5-Bromo-2-(6-methylpyrid-2-ylmethylamino)-4-(5-methyl-1H-pyrazol-3-ylamino)pyrimidine | 2.12(s, 3H), 2.45(s, 3H), 4.48(s, 1H), 6.00(br s, 1H), 7.08(d, 2H), 7.55(t, 1H), 8.00(s, 1H) | 374 | Meth 1 | Meth 95 |
| 90 | 5-Bromo-2-(5,6-dimethylpyrid-2-ylmethylamino)-4-(5-methyl-1H-pyrazol-3-ylamino)pyrimidine | 2.10(s, 3H), 2.18(s, 3H), 2.40(s, 3H), 4.45(s, 2H), 6.10(br s, 1H), 7.03(d, 1H), 7.45(d, 1H), 7.98(s, 1H) | 388 | Meth 1 | Meth 96 |
| 91 | 5-Chloro-2-(3-methylisoxazol-5-ylmethylamino)-4-(5-isopropyl-1H-pyrazol-3-ylamino)pyrimidine | 1.20(d, 6H), 2.15(s, 3H), 2.88(m, 1H), 4.50(s, 2H), 6.08(s, 1H), 6.30(s, 1H), 7.95(s, 1H) | 348 | Meth 19 | |
| 92 | 5-Bromo-4-(5-methyl-1H-pyrazol-3-ylamino)-2-[1-(pyrid-2-yl)ethylamino]pyrimidine | 1.45(d, 3H), 2.15(s, 3H), 5.00(s, 1H), 5.95(br s, 1H), 7.18(m, 1H), 7.35(d, 1H), 7.68(t, 1H), 7.95(s, 1H), 8.50(d, 1H) | 374 | Meth 1 | Meth 91 |
| 93 | 5-Bromo-4-(5-methyl-1H-pyrazol-3-ylamino)-2-[1-(pyrid-3-yl)ethylamino]pyrimidine | 1.45(d, 3H), 2.17(s, 3H), 4.98(s, 1H), 6.00(br s, 1H), 7.30(m, 1H), 7.75(d, 1H), 7.93(s, 1H), 8.38(d, 1H), 8.55(s, 1H) | 374 | Meth 1 | Meth 90 |
| 94 | 5-Chloro-4-(5-methyl-1H-pyrazol-3-ylamino)-2-[1-(pyrid-3-yl)ethylamino]pyrimidine | 1.45(d, 3H), 2.18(s, 3H), 5.00(s, 1H), 6.00(br s, 1H), 7.33(m, 1H), 7.75(d, 1H), 7.90(s, 1H), 8.38(m, 1H), 8.56(s, 1H) | 330 | Meth 10 | Meth 90 |

-continued

| Ex | Compound | NMR | m/z | SM1 | SM2 |
|---|---|---|---|---|---|
| 95 | 5-Bromo-4-(5-methyl-1H-pyrazol-3-ylamino)-2-[1-(pyrid-2-yl)propylamino]pyrimidine | 0.88(t, 3H), 1.85(m, 2H), 2.18(s, 3H), 4.80(s, 1H), 6.00(br s, 1H), 7.20(m, 1H), 7.33(d, 1H), 7.69(t, 1H), 7.95(s, 1H), 8.45(d, 1H) | 388 | Meth 1 | Meth 92 |
| 96 | 5-Chloro-4-(5-methyl-1H-pyrazol-3-ylamino)-2-[1-(pyrid-2-yl)propylamino]pyrimidine | 0.87(t, 3H), 1.80(m, 2H), 2.19(s, 3H), 4.83(s, 1H), 6.00(br s, 1H), 7.18(m, 1H), 7.33(d, 1H), 7.67(t, 1H), 7.87(s, 1H), 8.47(d, 1H) | 344 | Meth 10 | Meth 92 |
| 97 | 5-Bromo-4-(5-methyl-1H-pyrazol-3-ylamino)-2-[1-(pyrid-3-yl)propylamino]pyrimidine | 0.85(t, 3H), 1.73(m, 2H), 2.15(s, 3H), 4.73(s, 1H), 6.00(br s, 1H), 7.30(m, 1H), 7.70(d, 1H), 7.93(s, 1H), 8.35(d, 1H), 8.50(s, 1H) | 388 | Meth 1 | Meth 93 |
| 98 | 5-Chloro-4-(5-methyl-1H-pyrazol-3-ylamino)-2-[1-(pyrid-3-yl)propylamino]pyrimidine | 0.89(t, 3H), 1.77(m, 2H), 2.20(s, 3H), 4.78(s, 1H), 6.05(br s, 1H), 7.30(t, 1H), 7.75(d, 1H), 7.85(s, 1H), 8.38(d, 1H), 8.52(s, 1H) | 344 | Meth 10 | Meth 93 |
| 99 | 5-Bromo-2-(3-bromopyrid-5-ylmethylamino)-4-(5-methyl-1H-pyrazol-3-ylamino)pyrimidine | 1.19(s, 3H), 4.43(d, 2H), 6.02(br s, 1H), 7.65(t, 1H), 7.90(s, 1H), 8.04(s, 1H), 8.46(s, 1H), 8.55(s, 1H), 12.10(br s, 1H) | 440 | Meth 1 | WO 99/00385 |
| 100[11] | 5-Bromo-2-[2-(1-methylpyrrol-2-yl)ethylamino]-4-(5-tert-butyl-1H-pyrazol-3-ylamino)pyrimidine | 1.48(s, 9H), 3.07(t, 2H), 3.71(s, 3H), 3.80(m, 2H), 6.07(s, 1H), 6.13(t, 1H), 6.74(m, 2H), 8.17(s, 1H) | 418 | Meth 12 | Tetrahedron 1999 (55), 11619-11640 |
| 101 | 5-Bromo-2-[2-(pyrimidin-5-yl)ethylamino]-4-(5-tert-butyl-1H-pyrazol-3-ylamino)pyrimidine | 1.26(s, 9H), 2.92(m, 2H), 3.62(t, 2H), 6.38(s, 1H), 8.35(s, 1H), 8.73(s, 2H), 9.14(s, 1H) | 417 | Meth 12 | J Am Chem Soc, 1950, 72, 3539[12] |
| 102 | 5-Chloro-2-(pyrid-3-ylmethylamino)-4-(5-propyl-1H-pyrazol-3-ylamino)pyrimidine | 0.84(t, 3H), 1.50(m, 2H), 2.45(m, 2H), 4.46(s, 2H), 6.18(br s, 1H), 7.30(t, 1H), 7.67(d, 1H), 7.91(s, 1H), 8.38(d, 1H), 8.48(s, 1H) | 344 | Meth 16 | |
| 103 | 5-Chloro-4-(5-isopropyl-1H-pyrazol-3-ylamino)-2-(pyrid-3-ylmethylamino)pyrimidine | 1.13(d, 6H), 2.84(m, 1H), 4.47(s, 2H), 6.24(br s, 1H), 7.29(t, 1H), 7.65(d, 1H), 7.92(s, 1H), 8.39(d, 1H), 8.49(s, 1H) | 344 | Meth 19 | |
| 104 | 5-Bromo-2-[3-(methoxycarbonyl)isoxazol-5-ylmethylamino]-4-(5-methyl-1H-pyrazol-3-ylamino)pyrimidine | 2.17(s, 3H), 3.84(s, 3H), 4.59(s, 2H), 6.21(br s, 1H), 6.58(s, 1H), 8.03(s, 1H) | 408 | Meth 1 | Meth 74[13] |
| 105 | 5-Bromo-2-[3-(pyrrolidin-1-ylcarbonyl)isoxazol-5-ylmethylamino]-4-(5-methyl-1H-pyrazol-3-ylamino)pyrimidine | 1.86(m, 4H), 2.18(s, 3H), 3.44(t, 2H), 3.57(t, 2H), 4.58(s, 2H), 6.20(br s, 1H), 6.44(s, 1H), 8.04(s, 1H) | 447 | Meth 1 | Meth 78 |
| 106 | 5-Bromo-2-[3-(hydroxymethyl)isoxazol-5-ylmethylamino]-4-(5-methyl-1H-pyrazol-3-ylamino)pyrimidine | 2.17(s, 3H), 4.40(s, 2H), 4.50(s, 2H), 6.17(s, 1H), 6.28(br s, 1H), 8.02(s, 1H) | 380 | Meth 1 | Meth 76 |

[1]Heated for 12 hours.
[2]Heated for 24 hours.
[3]Reaction treated with 2M NH$_3$/MeOH to pH 9. Precipitate was filtered and washed with distilled water and diethyl ether.
[4]No aqueous work-up, product precipitates from DCM.
[5]No chromatography necessary.
[6]500 MHz (393 K).
[7]NMR run with no d4 acetic acid.
[8]NMR run at 373 K/400 MHz.
[9]NMR run with no d4 acetic acid at 343 K.
[10]NMR: Trifluorodeuterated acetic acid-d$_1$ use in place of acetic aicd-d$_4$.
[11]NMR run in CD$_3$OD.
[12]Compound could be prepared by the procedure described in this paper.
[13]Ester exchange with the methanol used in the chromatography occurred.

Example 107

5-Bromo-2-(3-carbamoylisoxazol-5-ylmethylamino)-4-(5-methyl-1H-pyrazol-3-ylamino)pyrimidine 5-Bromo-2-[3-(methoxycarbonyl)isoxazol-5-ylmethylamino]-4-(5-methyl-1H-pyrazol-3-ylamino)pyrimidine (Example 104; 50 mg, 0.11 mmol) was suspended in 7N methanolic ammonia (5 ml) and stirred at ambient temperature for 18 hours. The volatiles were removed by evaporation and the residue was triturated with DCM/diethyl ether (50:50) and the product collected by filtration to give the title compound (35 mg, 76%). NMR (DMSO): 2.18 (s, 3H), 4.57 (d, 2H), 6.28 (br s, 1H), 6.50 (s, 1H), 7.72 (s, 2H), 8.01 (s, 1H), 8.05 (s, 1H), 12.06 (s, 1H); m/z 393 (MH)$^+$.

Preparation of Starting Materials:—

The starting materials for the examples above are either commercially available or are readily prepared by standard methods from known materials. For example, the following reactions are an illustration, but not a limitation, of some of the starting materials used in the above reactions.

Method 1

5-Bromo-2-chloro-4-(5-methyl-1H-pyrazol-3-ylamino)pyrimidine

A solution of 5-bromo-2,4-dichloropyrimidine (10.0 g, 44 mmol), 3-amino-5-methyl-1H-pyrazole (6.0 g, 62 mmol) and N,N-diisopropylethylamine (9.20 ml, 53 mmol) in 1-butanol (80 ml) was heated at 85° C. for 12 hours. The mixture was allowed to cool to ambient temperature and the resulting precipitate collected by filtration. The solid product was washed with ethanol and dried to give the sub-titled compound (10.8 g, 85%). $^1$H NMR (DMSO): δ 2.23 (s, 3H), 6.23 (s, 1H), 8.39 (s, 1H), 9.21 (s, 1H), 12.27 (s, 1H); MS: m/z 290 (MH)$^+$.

Method 2

2-Oxobutylnitrile

Acetonitrile (13.7 ml, 260 mmol) was added to a suspension of sodium hydride (10.4 g of a 60% suspension in mineral oil, 260 mmol) in ethyl propionate (22.3 g, 220 mmol) and anhydrous 1,4-dioxane (200 ml) at ambient temperature. The mixture was heated at 100° C. for 12 hours and then allowed to cool. Water was added, the mixture adjusted to pH 2.0 with concentrated hydrochloric acid and extracted with DCM. The extracts were combined dried (MgSO$_4$) and the volatiles removed by evaporation. The residue was purified by column chromatography on silica gel eluting with DCM to give the title compound (20 g, 94%) as an oil. NMR (CDCl$_3$): 1.10 (t, 3H), 2.65 (q, 2H), 3.50 (s, 2H).

Methods 3-5

The following compounds were prepared by the procedure of Method 2 using the appropriate starting materials.

| Method | Compound |
|---|---|
| 3 | 2-Cyclopropyl-2-oxoethylnitrile |
| 4 | 2-Oxopentylnitrile |
| 5 | 2-Oxo-3-methylbutylnitrile |

Method 6

3-Amino-5-ethyl-1H-pyrazole

Hydrazine monohydrate (11.3 g, 230 mmol) was added to a solution of 3-oxobutyronitrile (Method 2; 20.0 g, 210 mmol) in ethanol (50 ml) and the mixture heated at 70° C. for 12 hours. The volatiles were removed by evaporation and the residue was purified by column chromatography on silica gel eluting with DCM/methanol (90:10) to give the title compound as an oil. (10.2 g, 44%). NMR (DMSO): 1.10 (t, 3H), 2.40 (q, 2H), 5.15 (s, 1H); m/z 112 (MH)$^+$.

Methods 7-9

The following compounds were prepared by the procedure of Method 6 using the appropriate starting materials.

| Method | Compound | SM |
|---|---|---|
| 7 | 3-Amino-5-cyclopropyl-1H-pyrazole | Method 3 |
| 8 | 3-Amino-5-propyl-1H-pyrazole | Method 4 |
| 9 | 3-Amino-5-isopropyl-1H-pyrazole | Method 5 |

Method 10

2,5-Dichloro-4-(5-methyl-1H-pyrrazol-3-ylamino)pyrimidine

A solution of 2,4,5-trichloropyrimidine (6.0 g, 32.6 mmol), 3-amino-5-methyl-1H-pyrrazole (3.18 g, 32.7 mmol) and N,N-diisopropylethylamine (6.30 ml, 36.2 mmol) in 1-butanol (50 ml) was heated at 100° C. for 2 hours. The volatiles were removed by evaporation and the residue was triturated with DCM to afford the title compound (5.7 g, 72%) as a white solid. NMR (DMSO): 2.23 (s, 3H), 6.23 (s, 1H), 8.39 (s, 1H), 9.21 (s, 1H), 12.27 (s, 1H); m/z 290 (MH)$^+$.

Methods 11-21

The following compounds were prepared by the procedure of Method 10 using the appropriate starting materials.

| Meth | Compound | SM |
|---|---|---|
| 11 | 5-Bromo-2-chloro-4-(5-cyclopropyl-1H-pyrazol-3-ylamino)pyrimidine | Meth 7 |
| 12 | 5-Bromo-2-chloro-4-(5-tert-butyl-1H-pyrazol-3-ylamino)pyrimidine | |
| 13 | 2,5-Dichloro-4-(5-tert-butyl-1H-pyrazol-3-ylamino)pyrimidine | |
| 14 | 5-Bromo-2-chloro-4-(5-ethyl-1H-pyrazol-3-ylamino)pyrimidine | Meth 6 |
| 15 | 4-(5-Methyl-1H-pyrazol-3-ylamino)-2-chloropyrimidine | |
| 16 | 2,5-Dichloro-4-(5-propyl-1H-pyrazol-3-ylamino)pyrimidine | Meth 8 |

-continued

| Meth | Compound | SM |
|---|---|---|
| 17 | 2,5-Dichloro-4-(5-ethyl-1H-pyrazol-3-ylamino)pyrimidine | Meth 6 |
| 18 | 5-Bromo-4-(5-propyl-1H-pyrazol-3-ylamino)-2-chloropyrimidine | Meth 8 |
| 19 | 2,5-Dichloro-4-(5-isopropyl-1H-pyrazol-3-ylamino)pyrimidine | Meth 9 |
| 20 | 2,5-Dichloro-4-(5-cyclopropyl-1H-pyrazol-3-ylamino)pyrimidine | Meth 7 |
| 21 | 5-Bromo-4-(5-isopropyl-1H-pyrazol-3-ylamino)-2-chloropyrimidine | Meth 9 |

Method 22

α-Chlorobenzaldehyde oxime

N-chlorosuccinimide (5.50 g, 41.3 mmol) was added in portions to a solution of benzaldehyde oxime (5.0 g, 41.3 mmol) in DMF (34 ml) such that the temperature did not rise above 35° C. The mixture was stirred at ambient temperature for 2 hours and then cooled with an ice bath. Water was added and the aqueous mixture extracted with ether. The organics were combined, washed with water and brine, dried (MgSO$_4$) and the solvent removed by evaporation to give the title compound (6.43 g, 100%) as an oil. NMR (CDCl$_3$): 7.4 (m, 3H), 7.8 (d, 2H), 8.9 (bs, 1H).

Methods 23-33

The following compounds were prepared by the procedure of Method 22 using the appropriate starting materials.

| Method | Compound | SM |
|---|---|---|
| 23 | 1-chloro-2-methylpropylaldehyde oxime | |
| 24 | α-Chloro-2-methoxybenzaldehyde oxime | |
| 25 | α-Chloro-2-chlorobenzaldehyde oxime | Method 36 |
| 26 | α-Chloro-2-fluorobenzaldehyde oxime | Method 37 |
| 27 | α-Chloro-2-trifluoromethoxybenzaldehyde oxime | Method 38 |
| 28 | α-Chloro-2-ethoxybenzaldehyde oxime | Method 39 |
| 29 | α-Chloro-2-trifluoromethylbenzaldehyde oxime | Method 40 |
| 30 | α-Chloro-2-methylbenzaldehyde oxime | Method 41 |
| 31 | α-Chloro-2-bromobenzaldehyde oxime | |
| 32 | α-Chloro-2-methoxypyrid-3-ylcarbaldehyde oxime | J.Chem. Soc. Perkin Trans 1 1990 2409-15. |
| 33 | α-Chloro-3-methoxybenzaldehyde oxime | Method 35 |

Method 34

α-Chloro-pyrid-3-ylcarbaldehyde oxime was prepared according to the method described in Tetrahedron 2000, 56, 1057-1064.

Method 35

3-Methoxybenzaldehyde oxime

A solution of hydroxylamine hydrochloride (10 g, 0.144 mol) in distilled water (20 ml) was added to 20%(w/v) aqueous sodium hydroxide solution (28 ml). 3-Methoxybenzaldehyde (14 ml, 0.12 mol) was added in one portion and the mixture was stirred for 2 hours at 0-5° C. The mixture was adjusted to pH7 and extracted with dichloromethane. The extracts were combined, dried (MgSO$_4$) and the solvent removed by evaporation to give the title compound (18.7 g, 100%) as a colourless oil. NMR (CDCl$_3$): 3.8 (s, 3H), 6.9 (m, 1H), 7.1 (m, 2H), 7.15 (m, 1H), 8.1 (s, 1H), 8.6 (br s, 1H).

Methods 36-42

The following compounds were prepared by the procedure of Method 35 using the appropriate starting materials.

| Method | Compound |
|---|---|
| 36 | 2-chlorobenzaldehyde oxime |
| 37 | 2-fluorobenzaldehyde oxime |
| 38 | 2-trifluoromethoxybenzaldehyde oxime |
| 39 | 2-ethoxybenzaldehyde oxime |
| 40 | 2-trifluoromethylbenzaldehyde oxime |
| 41 | 2-methylbenzaldehyde oxime |
| 42 | 2-iodobenzaldehyde oxime |

Method 43

5-(tert-Butoxycarbonylaminomethyl)-3-phenylisoxazole

A solution of α-chlorobenzaldehyde oxime (Method 22; 1 g, 6.4 mmol) in THF (13 ml) was added dropwise to a solution of N-tert-butoxycarbonyl-propargylamine (0.5 g, 3.2 mmol) and triethylamine (0.9 ml, 6.4 mmol) in THF (25 ml) cooled with an ice bath. The mixture was allowed to warm to ambient temperature and stirred for 2 days. The volatiles were removed by evaporation and the residue dissolved in DCM. The solution was washed with water and brine, dried (MgSO$_4$) and the solvent removed by evaporation. The residue was triturated with isohexane/ether (9:1) and collected by filtration to give the title compound (473 mg, 54%). NMR (CDCl$_3$) 1.45 (s, 9H), 4.45 (d, 2H), 5.10 (bs, 1H), 6.5 (s, 1H), 7.42 (m, 3H), 7.8 (m, 2H).

Methods 44-55

The following compounds were prepared by the procedure of Method 43 using the appropriate starting materials.

| Meth | Compound | SM |
|---|---|---|
| 44 | 5-(tert-Butoxycarbonylaminomethyl)-3-isopropylisoxazole | Meth 23 |
| 45 | 5-(tert-Butoxycarbonylaminomethyl)-3-(2-methoxyphenyl)isoxazole | Meth 24 |
| 46 | 5-(tert-Butoxycarbonylaminomethyl)-3-(2-chlorophenyl)isoxazole | Meth 25 |
| 47 | 5-(tert-Butoxycarbonylaminomethyl)-3-(2-fluorophenyl)isoxazole | Meth 26 |
| 48 | 5-(tert-Butoxycarbonylaminomethyl)-3-(2-trifluoromethoxyphenyl)isoxazole | Meth 27 |
| 49 | 5-(tert-Butoxycarbonylaminomethyl)-3-(2-ethoxyphenyl)isoxazole | Meth 28 |
| 50 | 5-(tert-Butoxycarbonylaminomethyl)-3-(2-trifluoromethylphenyl)isoxazole | Meth 29 |
| 51 | 5-(tert-Butoxycarbonylaminomethyl)-3-(2-methylphenyl)isoxazole | Meth 30 |
| 52 | 5-(tert-Butoxycarbonylaminomethyl)-3-(2-bromophenyl)isoxazole | Meth 31 |
| 53 | 5-(tert-Butoxycarbonylaminomethyl)-3-(2-methoxypyrid-3-yl)isoxazole | Meth 32 |
| 54 | 5-(tert-Butoxycarbonylaminomethyl)-3-(3-methoxyphenyl)isoxazole | Meth 33 |
| 55 | 5-(tert-Butoxycarbonylaminomethyl)-3-(pyrid-3-yl)isoxazole | Meth 34 |

Method 56

5-Aminomethyl-3-phenylisoxazole

Trifluoroacetic acid (1.7 ml, 2.6 mmol) was added dropwise to a solution of 5-(tert-butoxycarbonylaminomethyl)-3-phenylisoxazole (Method 43; 473 mg, 1.73 mmol) in DCM (8 ml) cooled in an ice bath. The mixture was warmed to ambient temperature and stirred for 18 hours and the volatiles removed by evaporation. The residue was triturated with ether to give the title compound (427 mg, 86%). NMR (DMSO) 4.33 (s, 2H), 7.1 (s, 1H), 7.5 (m, 3H), 7.8 (m, 2H), 8.6 (br s, 3H).

Methods 57-68

The following compounds were prepared by the procedure of Method 56 using the appropriate starting materials.

| Method | Compound | Method |
|---|---|---|
| 57 | 5-Aminomethyl-3-isopropylisoxazole | Method 44 |
| 58 | 5-Aminomethyl-3-(2-methoxyphenyl)isoxazole | Method 45 |
| 59 | 5-Aminomethyl-3-(2-chlorophenyl)isoxazole | Method 46 |
| 60 | 5-Aminomethyl-3-(2-fluorophenyl)isoxazole | Method 47 |
| 61 | 5-Aminomethyl-3-(2-trifluoromethoxyphenyl)isoxazole | Method 48 |
| 62 | 5-Aminomethyl-3-(2-ethoxyphenyl)isoxazole | Method 49 |
| 63 | 5-Aminomethyl-3-(2-trifluoromethylphenyl)isoxazole | Method 50 |
| 64 | 5-Aminomethyl-3-(2-methylphenyl)isoxazole | Method 51 |
| 65 | 5-Aminomethyl-3-(2-bromophenyl)isoxazole | Method 52 |
| 66 | 5-Aminomethyl-3-(2-methoxypyrid-3-yl)isoxazole | Method 53 |
| 67 | 5-Aminomethyl-3-(3-methoxyphenyl)isoxazole | Method 54 |
| 68 | 5-Aminomethyl-3-(pyrid-3-yl)isoxazole | Method 55 |

Method 69

5-(tert-Butoxycarbonylaminomethyl)-3-(pyrid-2-yl)isoxazole

Sodium hypochlorite (16 ml of a 14% w/v aqueous solution, 29.5 mmol) was added dropwise to a solution of 2-pyridinealdoxime (2 g, 16.4 mmol) and N-tert-butoxycarbonyl-propargylamine (5.6 g, 36.1 mmol) in DCM (30 ml) cooled in an ice bath. The mixture was stirred vigorously and allowed to warm to ambient temperature and stirred for 18 hours. The aqueous layer was separated and extracted with DCM. The combined organic extracts were combined, dried (MgSO$_4$) and the solvent removed by evaporation. The residue was purified by column chromatography on silica gel eluting with diethyl ether/isohexane (1:1) to give the title compound (1.93 g, 43%). NMR (CDCl$_3$) 1.45 (s, 9H), 4.5 (m, 2H), 5.03 (bs, 1H), 6.8 (s, 1H), 7.35 (m, 1H), 7.8 (m, 1H), 8.05 (d, 1H), 8.67 (m, 1H).

Method 70

5-Aminomethyl-3-(pyrid-2-yl)isoxazole 5-(tert-Butoxycarbonylaminomethyl)-3-(pyrid-2-yl)isoxazole (Method 69) was treated as described in Method 56 to give 5-aminomethyl-3-(2-pyridyl)isoxazole. NMR (DMSO) 4.38 (s, 2H), 7.1 (s, 1H), 7.5 (m, 1H), 7.95 (m, 2H), 8.65 (br s, 3H), 8.7 (m, 1H).

Method 71

3-Methyl-5-(1-phthalamidoethyl)isoxazole

A solution of triethylamine (0.35 ml, 2.5 mmol) in toluene (15 ml) was added dropwise to a solution of phenylisocyanate (5.43 ml, 50 mmol), nitroethane (2.15 ml, 30 mmol) and N-(but-1-yn-3-yl)phthalamide (5.0 g, 25 mmol) in toluene (65 ml) at ambient temperature. The mixture was stirred for 18 hours, filtered and the volatiles removed by evaporation. The residue was triturated with ether and the product collected by filtration to give the title compound (5.35 g, 89%). NMR (CDCl$_3$): 1.88 (d, 3H), 2.27 (s, 3H), 5.60 (q, H), 6.11 (s, H), 7.69-7.75 (m, 2H), 7.79-7.85 (m, 2H); m/z 257 (MH)$^+$.

Method 72

5-(1-aminoethyl)-3-methylisoxazole

A mixture of the 3-methyl-5-(1-phthalamidoethyl)isoxazole (Method 71; 3.55 g, 13.9 mmol), hydrazine monohydrate (0.75 ml, 15.3 mmol) and ethanol (50 ml) was heated at reflux for 4 hours. The mixture was allowed to cool to ambient temperature and glacial acetic acid (8.8 ml, 153 mmol) added, the mixture then heated at reflux for 2 hours. The mixture was allowed to cool to ambient temperature and the mixture neutralized with 50% aqueous sodium hydroxide solution, diluted with water and extracted with DCM, and the combined extracts washed with water followed by brine. The organics were separated, dried (MgSO$_4$) and the solvent removed by evaporation. The residue was dissolved in ethanol and treated with an excess of 1N ethereal hydrogen chloride, the volatiles removed by evaporation to give the title compound (1.52 g, 87%). NMR (DMSO): 1.46 (dd, 3H), 2.20 (m, 3H), 4.39 (q H), 6.38 (s, 1H), 6.60 (br s, 3H); m/z 127 (MH)$^+$.

Method 73

3-Ethoxycarbonyl-5-[N-(tert-butyloxycarbonyl)aminomethyl]isoxazole

A solution of ethyl chlorooximidoacetate (10 g, 66 mmol) in THF (200 ml) was added dropwise over 3 hours to a mixture of N-(tert-butyloxycarbonyl)propargylamine (20.5 g, 131 mmol) and triethylamine (11.2 ml, 80 mmol) in tetrahyrofuran (100 ml). The mixture was stirred at ambient temperature for 18 hours and then the volatiles were removed by evaporation. The residue was dissolved in DCM and washed with water followed by brine. The organics were separated, dried ($MgSO_4$) and the solvent removed by evaporation. The residue was purified by column chromatography on silica gel eluting with isohexane/diethyl ether (80:20 then 50:50) to give the title compound (10.6 g, 60%). NMR (DMSO): 1.3 (t, 3H), 1.38 (s, 9H), 4.35 (m, 2H), 6.62 (s, 1H), 7.55 (s, 1H); m/z 269 (M–H)—.

Method 74

3-Ethoxycarbonyl-5-aminomethylisoxazole

Trifluoroacetic acid (2.1 ml, 29 mmol) was added to a solution of 3-ethoxycarbonyl-5-[N-(tert-butyloxycarbonyl)aminomethyl]isoxazole (Method 73; 790 mg, 2.9 mmol) in DCM (15 ml). The mixture was stirred at ambient temperature for 4 hours then the volatiles removed by evaporation. The residue was triturated with diethyl ether to give the title compound (763 g, 93%). NMR (DMSO): 1.31 (t, 3H), 4.37 (m, 2H), 6.97 (s, 1H), 8.64 (s, 3H); m/z 171 $(MH)^+$.

Method 75

3-Hydroxymethyl-5-[N-(tert-butyloxycarbonyl)aminomethyl]isoxazole

Sodium borohydride (610 mg, 16 mmol) was added in portions to a solution of 3-ethoxycarbonyl-5-[N-(tert-butyloxycarbonyl)aminomethyl]isoxazole (Method 73; 1.62 g, 6 mmol) in ethanol (15 ml) at 0° C. under a nitrogen atmosphere. The mixture was stirred at ambient temperature for 4 hours then quenched with saturated aqueous sodium hydrogen carbonate solution. The mixture was extracted with EtOAc and the organics washed with brine then dried ($MgSO_4$). The solvent was removed by evaporation to give the title compound (1.25 g, 91%). NMR (DMSO): 1.38 (s, 9H), 4.21 (d, 2H), 4.44 (s, 2H), 5.40 (br s, 1H), 6.21 (s, 1H), 7.49 (br s, 1H); m/z 229 $(MH)^+$.

Method 76

3-Hydroxymethyl-5-aminomethylisoxazole

Trifluoroacetic acid (4 ml, 54 mmol) was added to a solution of 3-hydroxymethyl-5-[N-(tert-butyloxycarbonyl)aminomethyl]isoxazole (Method 75; 1.25 g, 5.4 mmol) in DCM (40 ml). The mixture was stirred at ambient temperature for 18 hours then the volatiles removed by evaporation. The residue was purified by chromatography on a SCX-2 column (50 g) eluting with methanol then 7N ammonia in methanol to give the title compound (676 mg, 96%). NMR (DMSO): 1.97 (br s, 2H), 3.76 (s, 2H), 4.44 (s, 2H), 5.38 (s, 1H), 6.26 (s, 1H).

Method 77

3-(Pyrrolidin-1-ylcarbonyl)-5-[N-(tert-butyloxycarbonyl)aminomethyl]isoxazole 3-Ethoxycarbonyl-5-[N-(tert-butyloxycarbonyl)aminomethyl]isoxazole (Method 73; 500 mg, 1.85 mmol) was dissolved in pyrrolidine (4 ml) and the mixture heated for 3 hours at 85° C. The volatiles were removed by evaporation and the residue was triturated with diethyl ether to give the title compound (432 mg, 79%) as a white solid. NMR (DMSO): 1.38 (s, 9H), 1.85 (m, 4H), 3.50 (t, 2H), 3.62 (t, 2H), 4.29 (d, 2H), 6.47 (1H), 7.53 (s, 1H); m/z 240 $(M-C_4H_8)^+$.

Method 78

3-(Pyrrolidin-1-ylcarbonyl)-5-aminomethyl]isoxazole 3-(Pyrrolidin-1-ylcarbonyl)-5-[N-(tert-butyloxycarbonyl)aminomethyl]isoxazole (Method 77) was deprotected as described in Method 74 to give the title compound as its trifluoroacetate salt (428 mg, 95%). NMR (DMSO): 1.88 (m, 4H), 3.49 (t, 2H), 3.63 (t, 2H), 4.35 (s, 2H), 6.83 (s, 1H), 8.58 (s, 3H); m/z 196 $(MH)^+$.

Method 79

5-[N-(tert-Butoxycarbonyl)aminomethyl]-3-(2-iodoophenyl)isoxazole

2-Iodobenzaldehyde oxime (Method 42) was treated as described in Methods 22 and 43 to give the title compound.

Method 80

5-[N-(tert-Butoxycarbonyl)aminomethyl]-3-(2-cyanophenyl)isoxazole

Copper (I) cyanide (2.49 g, 27.8 mmol), tetra-n-butylammoniumcyanide (1.87 g, 6.95 mmol), tris(dibenzylideneacetone)dipalladium(0) (0.247 g, 0.28 mmol) and diphenylphosphinoferrocene (0.619 g, 1.12 mmol) were added to a degassed solution of 5-[N-(tert-butoxycarbonyl)aminomethyl]-3-(2-iodophenyl)isoxazole (Method 79; 2.78 g, 6.95 mmol) in 1,4-dioxan (35 ml) under nitrogen. The mixture was heated at reflux for 3 hours, cooled to ambient temperature, diluted with EtOAc and filtered through diatomaceous earth. The filtrate was washed with saturated aqueous sodium hydrogen carbonate solution and brine, dried ($MgSO_4$) and the solvent was removed by evaporation. The residue was purified by column chromatography on silica gel eluting with EtOAc/isohexanes (15:85 increasing in polarity to 25:75) to give the title compound (1.29 g, 62%). NMR ($CDCl_3$): 1.49 (s, 9H), 4.52 (d, 2H), 5.09 (br s, H), 6.81 (s, H), 7.55 (t, H), 7.70 (t, H), 7.79 (d, H), 7.95 (d, H); m/z 300 $(MH)^+$.

Method 81

5-Aminomethyl-3-(2-cyanophenyl)isoxazole

5-[N-(tert-Butoxycarbonyl)aminomethyl]-3-(2-cyanophenyl)isoxazole (Method 80; 1.28 g, 4.28 mmol) was treated as described in Method 56 to give the title compound (1.34 g, 100%). NMR (DMSO): 4.45 (s, 2H), 7.17 (s, H), 7.73 (dd, H), 7.85-7.95 (m, 2H), 8.62 (br s, 3H); m/z 200 $(MH)^+$.

Method 82

3-Methyl-5-{2-[bis-(N-tert-butoxycarbonyl)amino]ethyl}isoxazole

Bis-N-tert-butoxycarbonyl-3-butyne as synthesised in *J. Am. Chem. Soc.* 1987 (109), 2765 (2.2 g, 8.2 mmol), was treated as described in Method 71 to give the title compound (0.59 g, 22%). NMR (CDCl$_3$): 1.49 (s, 18H), 2.24 (s, 3H), 3.00 (t, 2H), 3.88 (t, 2H), 5.85 (s, H).

Method 83

3-Methyl-5-(2-aminoethyl)isoxazole

Trifluoroacetic acid (2.5 ml, 3.8 mmol) was added dropwise to a solution of 3-methyl-5-{2-[bis-(N-tert-butoxycarbonyl)amino]ethyl}isoxazole (Method 82; 0.589 g, 1.8 mmol) in DCM (10 ml) cooled at 0° C. The mixture was allowed to warm to ambient temperature and stirred for 48 hours. The volatiles were removed by evaporation and the residue was purified by chromatography on a SCX-2 ion exchange column eluting with methanol and then 7 N ammonia in methanol. The purified product was treated with an excess of 1.0M ethereal hydrogen chloride (3.5 ml) to give the title compound as its hydrochloride salt (0.24 g, 82%). NMR (DMSO) freebase: 2.18 (s, 3H), 2.71-2.79 (m, 2H), 2.80-2.88 (m, 2H), 6.10 (s, H).

Method 84

3-Azidomethyl-5-methylisoxazole

3-Chloromethyl-5-methylisoxazole (500 mg, 3.8 mmol) and sodium azide (494 mg, 7.6 mmol) were heated in DMF (10 ml) at 60° C. for 6 hours. The reaction mixture was diluted with water then extracted with EtOAc. The organic extracts were dried (MgSO$_4$) and the volatiles removed by evaporation to give the title compound (387 mg, 73%) as an oil. NMR (DMSO): 2.40 (s, 3H), 4.48 (s, 2H), 6.28 (s, 1H).

Method 85

3-Aminomethyl-5-methylisoxazole

3-Azidomethyl-5-methylisoxazole (Method 84; 384 mg, 2.8 mmol) and polystyrene polymer supported triphenylphosphine (4.2 g, 4.2 mmol) were stirred together in a mixture of THF (17 ml) and distilled water (0.58 ml) for 24 hours. The reaction mixture was filtered, the resin washed with diethyl ether and then DCM. The combined filtrates were evaporated and the residue purified on a SCX-2 column eluting with methanol followed by 7N methanolic ammonia to give the title compound (211 mg, 67%) as an oil. NMR (DMSO): 1.93 (br s, 2H), 2.34 (s, 3H), 3.63 (s, 2H), 6.17 (s, 1H).

Method 86

α-Methyl-pyridin-3-ylcarbaldehyde oxime

Hydroxylamine hydrochloride (9.46 g, 136.2 mmol) was added to a solution of 3-acetylpyridine (11.02 g, 90.7 mmol) in methanol (100 ml) and the reaction mixture heated at reflux for 30 minutes. The volatiles were removed by evaporation and the residue dissolved in water. The solution was cooled to 0° C. and basified with 2N aqueous sodium hydroxide solution to pH 12 and the mixture then extracted with EtOAc. The extracts were combined, washed with saturated brine and dried (Na$_2$SO$_4$). The solvent was removed by evaporation to give the title product (11.6 g, 94%) as a solid. NMR (DMSO): 2.20 (s, 3H), 7.40 (m, 1H), 8.00 (m, 1H), 8.55 (d, 1H), 8.85 (s, 1H) 11.43 (s, 1H). m/z: 137 (MH)$^+$.

Methods 87-89

The following compounds were prepared by the procedure of Method 86 using the appropriate starting materials.

| Method | Compound |
| --- | --- |
| 87 | α-Methyl-pyridin-2-ylcarbaldehyde oxime |
| 88 | α-Ethyl-pyridin-2-ylcarbaldehyde oxime |
| 89 | α-Ethyl-pyridin-3-ylcarbaldehyde oxime |

Method 90

3-(1-Aminoethyl)pyridine

A 50% suspension of rainey nickel in water (1.1 g) was added to a solution of α-methyl-pyridin-3-ylcarbaldehyde oxime (Method 86; 10.6 g, 77.9 mmol) and 20% ethanolic ammonia (500 ml) and the reaction mixture hydrogenated with gaseous hydrogen at 40 psi and 40° C. until the theoretical volume of gas was consumed. The reaction mixture was filtered through a layer of diatomaceous earth and the filter pad washed with water and ethanol. The filtrate was removed by evaporation of give the title product. (8.05 g, 85%) as an oil. NMR (DMSO): 1.28 (d, 3H), 4.05 (m, 1H), 7.33 (t, 1H), 7.75 (d, 1H), 8.40 (d, 1H), 8.55 (s, 1H). m/z: 123 (MH)$^+$.

Methods 91-93

The following compounds were prepared by the procedure of Method 90 using the appropriate starting materials.

| Method | Compound | SM |
| --- | --- | --- |
| 91 | 2-(1-Aminoethyl)pyridine | Method 87 |
| 92 | 2-(1-Aminopropyl)pyridine | Method 88 |
| 93 | 3-(1-Aminopropyl)pyridine | Method 89 |

Method 94

2-Aminomethyl-6-chloropyridine

A 1M solution of lithium aluminium hydride in THF (2.88 ml, 2.88 mmol) was added dropwise to a solution of 6-chloro-2-cyanopyridine (532 mg, 3.84 mmol) in THF (10 ml) at −5° C. under an atmosphere of nitrogen. The mixture was stirred at −5° C. for two hours and the reaction quenched by careful, sequential addition of water (0.1 ml), 15% aqueous sodium hydroxide solution (0.1 ml) and then water (0.3 ml). The mixture was stirred for one hour at 0° C., the insolubles removed by filtration and the filter pad washed thoroughly with methanol. The resulting solution was evaporated and the residue purified by column chromatography on silica gel eluting with DCM/methanol/ammonia (95:5:0 increasing in polarity to 90:10:1) to give the title compound. (215 mg, 40%) as an oil. NMR (DMSO): 2.10 (br s, 2H), 3.75 (s, 2H), 7.30 (d, 1H), 7.55 (d, 1H), 7.80 (t, 1H).

Methods 95-97

The following compounds were prepared by the procedure of Method 94 using the appropriate starting materials.

| Method | Compound |
|---|---|
| 95 | 2-Aminomethyl-6-methylpyridine |
| 96[1] | 2-Aminomethyl-5,6-dimethylpyridine |
| 97 | 2-Aminomethyl-3-methylpyridine |

[1]SM Bioorg. Med. Chem. Lett. 1998, 453-8

Method 98

2-(N-Oxopyridin-4-yl)pyridine

3-Chloroperbenzoic acid (57%-86% active strength) (7.5 g, 43 mmol) was added in portions to a solution of 2-(pyridin-4-yl)pyridine (4.78 g, 30.6 mmol) in DCM (50 ml) at 0° C. After stirring for 2 hours sodium metabisulfite was added in portions until all excess peroxide was destroyed. The solids were removed by filtration and the filtrate was basified with solid potassium carbonate. The mixture was filtered, the filtrate evaporated and the residue purified by column chromatography on silica gel eluting with methanol/acetone (10:90) to give the title compound (4.2 g, 80%) as a white solid. NMR (DMSO): 7.41 (t, 1H), 7.92 (t, 1H), 8.10 (m, 3H), 8.30 (d, 2H), 8.70 (d, 1H); m/z 173 (MH)$^+$.

Method 99

2-(2-Cyanopyridin-4-yl)pyridine

Trimethylsilylcyanide (1.9 ml, 14.5 mmol) was added dropwise to a suspension of 2-(N-oxopyridin-4-yl)pyridine (Method 98; 1 g, 5.8 mmol) and triethylamine (1.2 ml, 8.7 mmol) in acetonitrile (5 ml). The mixture was heated at 110° C. for 18 hours, cooled to ambient temperature then diluted with aqueous saturated sodium hydrogen carbonate solution. The mixture was extracted with DCM, the extracts dried (MgSO$_4$) and the volatiles removed by evaporation. The residue was pre-adsorbed onto silica and purified by column chromatography on silica gel eluting with hexane:EtOAc (1:1). The purified product was triturated with diethyl ether to give the title compound (627 mg, 60%) as a white solid. NMR (DMSO): 7.54 (t, 1H), 8.01 (t, 1H), 8.25 (d, 1H), 8.40 (d, 1H), 8.66 (s, 1H), 8.77 (d, 1H), 8.87 (d, 1H).

Method 100

2-(2-Aminomethylpyridin-4-yl)pyridine 2-(2-Cyanopyridin-4-yl)pyridine (Method 99; 563 mg, 3.11 mmol) was dissolved in anhydrous THF (10 ml) under a nitrogen atmosphere and was cooled to 0° C. LiAlH$_4$ (2.3 ml of a 1M solution in THF, 2.3 mmol) was added dropwise and the reaction was stirred at 0° C. for 3 hours. The reaction was quenched with water (0.1 ml) followed by 15% sodium hydroxide solution (0.1 ml) then water (0.3 ml). The mixture was filtered and the filter pad was washed with methanol. The volatiles were removed from the filtrate by evaporation to give the title compound (570 mg, 99%) as a gum. m/z 186 (MH)$^+$ Method 101

2-(3-Cyanopyridin-5-yl)pyridine 2-(3-Bromopyridin-5-yl)pyridine (2 g, 10.9 mmol) in THF (10 ml) was added dropwise to a solution of 2-pyridylzincbromide (22 ml of a 0.5M solution in THF, 11 mmol) in THF (10 ml) under a nitrogen atmosphere. Tetrakis (triphenylphosphine)palladium(0) (630 mg, 0.54 mmol) was added and the reaction stirred at ambient temperature for 18 hours. The reaction was quenched with saturated aqueous ammonium chloride solution then the volatiles were removed by evaporation. The residue was suspended in water then extracted with DCM. The organic extracts were combined, washed with water then filtered through phase separating paper and the volatiles removed by evaporation. The residue was purified by column chromatography on silica gel eluting with hexane:EtOAc (2:1). The purified product was triturated with diethyl ether to give the title compound (0.98 g, 50%) as a white solid. NMR (DMSO): 7.47 (t, 1H), 7.97 (t, 1H), 8.15 (d, 1H), 8.75 (d, 1H), 8.90 (d, 1H), 9.07 (s, 1H), 9.53 (s, 1H); m/z 182 (MH)$^+$.

Method 102

2-(3-Aminomethylpyridin-5-yl)pyridine 2-(3-Cyanopyridin-5-yl)pyridine (Method 101; 0.98 g, 5.4 mmol) was dissolved in a mixture of ethanol (45 ml) and methanol (30 ml). Concentrated hydrochloric acid (1.2 ml) and 10% palladium on carbon catalyst (575 mg) were added and the mixture stirred under an atmosphere of hydrogen for 4 hours. The mixture was filtered through diatomaceous earth, the filter pad washed with ethanol and the volatiles removed from the filtrate by evaporation. The crude solid was suspended in a small volume of methanol and filtered to give the title compound (794 mg, 66%) as an orange solid. NMR (DMSO): 4.31 (m, 2H) 7.58 (t, 1H), 8.09 (t, 1H), 8.24 (d, 1H), 8.78 (d, 1H), 8.89 (bs, 2H), 9.03 (s, 1H), 9.26 (s, 1H), 9.43 (s, 1H); m/z 186 (MH)$^+$.

Pharmacological Analysis

Methods for Detecting Inhibition of Igf-1r Kinase Activity and Downstream Signalling and Selectivity Over Insulin Receptor Kinase and Egfr Signalling Abbreviations Used PBS (PBS/T) is Phosphate buffered saline, pH7.4 (with 0.05% Tween 20)

HEPES is N-[2-Hydroxyethyl]piperazine-N'-[2-ethanesulfonic acid]

DTT is dithiothreitol

TMB is tetramethyl benzidine

DMSO is dimethyl sulphoxide

BSA is bovine serum albumin

ATP is adenosine tri-phosphate

DMEM is Dulbecco's modified Eagle's Medium

FBS/FCS is foetal bovine/calf serum

HBSS is Hanks Balanced Salts Solution

HRP is horse-radish peroxidase

SDS is sodium dodecyl sulphate

IGF-I (IGF-1R) is insulin-like growth factor-I (IGF-1 receptor)

EGF is Epidermal growth factor

IGF-1R Kinase Assay a) Protein Cloning, Expression and Purification

A DNA molecule encoding a fusion protein containing glutathione-S-transferase (GST), thrombin cleavage site and IGF-1R intracellular domain (amino-acids 930-1367) and subsequently referred to as GST-IGFR, was constructed and cloned into pFastBac 1 (Life Technologies Ltd, UK) using standard molecular biology techniques (Molecular Cloning—A Laboratory Manual, Second Edition 1989; Sambrook, Fritsch and Maniatis; Cold Spring Harbour Laboratory Press).

Production of recombinant virus was performed following the manufacturer's protocol. Briefly, the pFastBac-1 vector containing GST-IGFR was transformed into E. coli DH10Bac cells containing the baculovirus genome (bacmid DNA) and via a transposition event in the cells, a region of the pFastBac vector containing gentamycin resistance gene and the GST-IGFR expression cassette including the baculovirus polyhedrin promoter was transposed directly into the bacmid DNA. By selection on gentamycin, kanamycin, tetracycline and X-gal, resultant white colonies should contain recombinant bacmid DNA encoding GST-IGFR. Bacmid DNA was extracted from a small scale culture of several BH10Bac white colonies and transfected into Spodoptera frugiperda Sf21 cells grown in TC100 medium (Life Technologies Ltd, UK) containing 10% serum using CellFECTIN reagent (Life Technologies Ltd, UK) following the manufacturer's instructions. Virus particles were harvested by collecting cell culture medium 72 hrs post transfection. 0.5 mls of medium was used to infect 100 ml suspension culture of Sf21s containing $1 \times 10^7$ cells/ml. Cell culture medium was harvested 48 hrs post infection and virus titre determined using a standard plaque assay procedure. Virus stocks were used to infect Sf9 and "High 5" cells at a multiplicity of infection (MOI) of 3 to ascertain expression of recombinant GST-IGFR.

The GST-IGFR protein was purified by affinity chromatography on Glutathione-Sepharose followed by elution with glutathione. Briefly, cells were lysed in 50 mM HEPES pH 7.5 (Sigma, H3375), 200 mM NaCl (Sigma, S7653), Complete Protease Inhibitor cocktail (Roche, 1 873 580) and 1 mM DTT (Sigma, D9779), hereinafter referred to as lysis buffer. Clarified lysate supernatant was loaded through a chromatography column packed with Glutathione Sepharose (Amersham Pharmacia Biotech UK Ltd.). Contaminants were washed from the matrix with lysis buffer until the UV absorbance at 280 nm returned to the baseline. Elution was carried out with lysis buffer containing 20 mM reduced glutathione (Sigma, D2804) and fractions containing the GST fusion protein were pooled and dialysed into a glycerol-containing buffer comprising 50 mM HEPES, pH 7.5, 200 mM NaCl, 10% glycerol (v/v), 3 mM reduced glutathione and 1 mM DTT.

b) Kinase Activity Assay

The activity of the purified enzyme was measured by phosphorylation of a synthetic poly GluAlaTyr (EAY) 6:3:1 peptide (Sigma-Aldrich Company Ltd, UK, P3899) using an ELISA detection system in a 96-well format b.i) Reagents Used

| Stock solutions | | | |
|---|---|---|---|
| 200 mM | HEPES, pH 7.4 | stored at 4° C. | (Sigma, H3375) |
| 1 M | DTT | stored at −20° C. | (Sigma, D9779) |
| 100 mM | $Na_3VO_4$ | stored at 4° C. | (Sigma, S6508) |
| 1 M | $MnCl_2$ | stored at 4° C. | (Sigma, M3634) |
| 1 mM | ATP | stored at −20° C. | (Sigma, A3377) |
| Neat | Triton X-100 | stored at room temperature | (Sigma, T9284) |
| 10 mg/ml | BSA | stored at 4° C. | (Sigma, A7888) |

Enzyme Solution
   GST-IGF-1R fusion protein at 75 ng/ml in 100 mM HEPES, pH 7.4, 5 mM DTT, 0.25 mM $Na_3VO_4$, 0.25% Triton X-100, 0.25 mg/ml BSA, freshly prepared.

Co-factor Solution
   100 mM HEPES, pH 7.4, 60 mM $MnCl_2$, 5 mM ATP

Poly EAY Substrate
   Sigma substrate poly (Glu, Ala, Tyr) 6:3:1 (P3899)
   Made up to 1 mg/ml in PBS and stored at −20° C.

Assay Plates
   Nunc Maxisorp 96 well immunoplates (Life Technologies Ltd, UK)

Antibodies
   Anti-phosphotyrosine antibody, monoclonal from Upstate Biotechnology Inc., NY, USA (UBI 05-321). Dilute 3 μl in 11 ml PBS/T+0.5% BSA per assay plate.
   Sheep-anti-mouse IgG HRP-conjugated secondary antibody from Amersham Pharmacia Biotech UK Ltd. (NXA931). Dilute 20 μl of stock into 11 ml PBS/T+0.5% BSA per assay plate.

TMB Solution
   Dissolve 1 mg TMB tablet (Sigma T5525) into 1 ml DMSO (Sigma, D8779) in the dark for 1 hour at room temperature. Add this solution to 9 ml of freshly prepared 50 mM phosphate-citrate buffer pH 5.0+0.03% sodium perborate [1 buffer capsule (Sigma P4922) per 100 ml distilled water].
   Stop solution is 1M $H_2SO_4$ (Fisher Scientific UK. Cat. No. S/9200/PB08).

Test Compound
   Dissolve in DMSO to 10 mM then dilutions in distilled water to give a range from 200 to 0.0026 μM in 1-2% DMSO final concentration in assay well.

b.ii) Assay Protocol
   The poly EAY substrate was diluted to 1 g/ml in PBS and then dispensed in an amount of 100 μl per well into a 96-well plate. The plate was sealed and incubated overnight at 4° C. Excess poly EAY solution was discarded and the plate was washed (2×PBS/T; 250 μl PBS per well), blotting dry between washes. The plate was then washed again (1×50 mM HEPES, pH 7.4; 250 μl per well) and blotted dry (this is important in order to remove background phosphate levels). 10 μl test compound solution was added with 40 μl of kinase solution to each well. Then 50 μl of co-factor solution were added to each well and the plate was incubated for 60 minutes at room temperature.

The plate was emptied (i.e. the contents were discarded) and was washed twice with PBS/T (250 µl per well), blotting dry between each wash. 100 µl of diluted anti-phosphotyrosine antibody were added per well and the plate was incubated for 60 minutes at room temperature.

The plate was again emptied and washed twice with PBS/T (250 µl per well), blotting dry between each wash. 100 µl of diluted sheep-anti-mouse IgG antibody were added per well and the plate was left for 60 minutes at room temperature. The contents were discarded and the plate washed twice with PBS/T (250 µl per well), blotting dry between each wash. 100 µl of TMB solution were added per well and the plate was incubated for 5-10 minutes at room temperature (solution turns blue in the presence horse radish peroxidase).

Reaction was stopped with 50 µl of $H_2SO_4$ per well (turns the blue solution yellow) and the plate was read at 450 nm in Versamax plate reader (Molecular Devices Corporation, CA, USA) or similar.

The compounds of the Examples were found to have an $IC_{50}$ in the above test of less than 100 µM.

Inhibition of IGF-stimulated Cell Proliferation

The construction of murine fibroblasts (NIH3T3) overexpressing human IGF-1 receptor has been described by Lammers et al (EMBO J, 8, 1369-1375, 1989). These cells show a proliferative response to IGF-I which can be measured by BrdU incorporation into newly synthesised DNA. Compound potency was determined as causing inhibition of the IGF-stimulated proliferation in the following assay:

a.i) Reagents Used:

Cell Proliferation ELISA, BrdU (calorimetric) [Boehringer Mannheim (Diagnostics and Biochemicals) Ltd, UK. Cat no. 1 647 229].

DMEM, FCS, Glutamine, HBSS (all from Life Technologies Ltd., UK).

Charcoal/Dextran Stripped FBS (HyClone SH30068.02, Perbio Science UK Ltd).

BSA (Sigma, A7888).

Human recombinant IGF-1 Animal/media grade (GroPep Limited ABN 78 008 176 298, Australia. Cat No. IU 100).

Preparation and Storage of IGF

100 µg of lyophilised IGF was reconstituted in 100 ul of 10 mM HCl.

Add 4001 µl of 1 mg/ml BSA in PBS

25 µl aliquots @ 200 µg/ml IGF-I

Stored at −20° C.

For Assay:

10 µl of stock IGF+12.5 ml growth medium to give 8× stock of 160 ng/ml.

Complete Growth Medium

DMEM, 10% FCS, 2 mM glutamine

Starvation Medium

DMEM, 1% charcoal/dextran stripped FCS, 2 mM glutamine

Test Compound

Compounds are initially dissolved in DMSO to 10 mM, followed by dilutions in DMEM+1% FCS+glutamine to give a range from 100 to 0.0.45 µM in 1-0.00045% DMSO final concentration in assay well.

a.ii) Assay Protocol

Day 1

Exponentially growing NIH3T3/IGFR cells were harvested and seeded in complete growth medium into a flat-bottomed 96 well tissue culture grade plate (Costar 3525) at $1.2 \times 10^4$ cells per well in a volume of 100 µl.

Day 2

Growth medium was carefully removed from each well using a multi-channel pipette. Wells were carefully rinsed three times with 200 µl with HBSS. 100 µl of starvation medium was added to each well and the plate was re-incubated for 24 hours.

Day 3

50 µl of a 4× concentrate of test compound was added to appropriate wells. Cells were incubated for 30 minutes with compound alone before the addition of IGF. For cells treated with IGF, an appropriate volume (ie. 25 µl) of starvation medium was added to make a final volume per well up to 200 µl followed by 25 µl of IGF-1 at 160 ng/ml (to give a final concentration of 20 ng/ml). Control cells unstimulated with IGF also had an appropriate volume (ie. 50 µl) of starvation medium added to make final volume per well up to 200 µl. The plate was re-incubated for 20 hours.

Day 4

The incorporation of BrdU in the cells (after a 4 h incorporation period) was assessed using the BrdU Cell Proliferation Elisa according to the manufacturer's protocol.

The compounds of the Examples were found to have an $IC_{50}$ in the above test of less than 50 µM.

Mechanism of Action Assay

Inhibition of IGF-IR mediated signal transduction was determined by measuring changes in phosphorylation of IGF-IR, Akt and MAPK (ERK1 and 2) in response to IGF-I stimulation of MCF-7 cells (ATCC No. HTB-22). A measure of selectivity was provided by the effect on MAPK phosphorylation in response to EGF in the same cell line.

a.i) Reagents Used:

RPMI 1640 medium, RPMI 1640 medium without Phenol Red, FCS, Glutamine (all from Life Technologies Ltd., UK)

Charcoal/Dextran Stripped FBS (HyClone SH30068.02, Perbio Science UK Ltd)

SDS (Sigma, $L^{4390}$)

2-mercaptoethanol (Sigma, M6250)

Bromophenol blue (Sigma, B5525)

Ponceau S (Sigma, P3504)

Tris base (TRIZMA™ base, Sigma, T1503)

Glycine (Sigma, G7403)

Methanol (Fisher Scientific UK. Cat. No. M/3950/21)

Dried milk powder (Marvel™, Premier Brands UK Ltd.)

Human recombinant IGF-1 Animal/media grade (GroPep Limited ABN 78 008 176 298, Australia. Cat No. IU 100).

Human recombinant EGF (Promega Corporation, WI, USA. Cat. No. G5021)

Complete Growth Medium

RPMI 1640, 10% FCS, 2 mM glutamine

Starvation Medium

RPM11640 medium without Phenol Red, 1% charcoal/dextran stripped FCS, 2 mM glutamine Test Compound Compounds were initially dissolved in DMSO to 10 mM, followed by dilutions in RPMI 1640 medium without Phenol Red+1% FCS+2 mM glutamine to give a range from 100 to 0.0.45 µM in 1-0.00045% DMSO final concentration in assay well.

Western Transfer Buffer 50 mM Tris base, 40 mM glycine, 0.04% SDS, 20% methanol

Laemmli Buffer ×2:

100 mM Tris-HCl pH6.8, 20% glycerol, 4% SDS

Sample Buffer ×4:

200 mM 2-mercaptoethanol, 0.2% bromophenol blue in distilled water.

Primary Antibodies

Rabbit anti-human IGF-1Rβ (Santa Cruz Biotechnology Inc., USA, Cat. No sc-713)

Rabbit anti-insulin/IGF-1R [pYpY$^{1162/1163}$] Dual Phosphospecific (BioSource International Inc, CA, USA. Cat No. 44-8041)

Mouse anti-PKBα/Akt (Transduction Laboratories, KY, USA. Cat. No. P67220)

Rabbit anti-Phospho-Akt (Ser473) (Cell Signalling Technology Inc, MA, USA. Cat. No.#9271)

Rabbit anti-p44/p42 MAP kinase (Cell Signalling Technology Inc, MA, USA. Cat. No.#9102)

Rabbit anti-Phospho p44/p42 MAP kinase (Cell Signalling Technology Inc, MA, USA. Cat. No.#9101)

Mouse anti-actin clone AC-40 (Sigma-Aldrich Company Ltd, UK, A4700)

| Antibody dilutions | | |
|---|---|---|
| Antibody | Dilution in PBST | Secondary antibody in PBST |
| IGFR | 1:200 with 5% milk | Anti-rabbit with 5% milk |
| Phospho-IGFR | 1:1000 with 5% milk | Anti-rabbit with 5% milk |
| Akt | 1:1000 with 5% milk | Anti-mouse with 5% milk |
| PhosphoAkt | 1:1000 with 5% milk | Anti-rabbit with 5% milk |
| MAPK | 1:1000 with 5% milk | Anti-rabbit with 5% milk |
| Phospho-MAPK | 1:1000 with 5% milk | Anti-rabbit with 5% milk |
| Actin | 1:1000 with 5% milk | Anti-mouse with 5% milk |

Secondary Antibodies

Goat anti-rabbit, HRP linked (Cell Signalling Technology Inc, MA, USA. Cat. No.#7074)

Sheep-anti-mouse IgG HRP-conjugated (Amersham Pharmacia Biotech UK Ltd. Cat. No. NXA931)

Dilute anti-rabbit to 1:2000 in PBST+5% milk

Dilute anti-mouse to 1:5000 in PBST+5% milk a.ii) Assay Protocol

Cell Treatment

MCF-7 cells were plated out in a 24 well plate at 1×10$^5$ cells/well in 1 ml complete growth medium. The plate was incubated for 24 hours to allow the cells to settle. The medium was removed and the plate was washed gently 3 times with PBS 2 ml/well. 1 ml of starvation medium was added to each well and the plate was incubated for 24 hours to serum starve the cells.

Then 25 μl of each compound dilution was added and the cells and compound were incubated for 30 minutes at 37° C. After 30 minutes incubation of the compound, 25 μl of IGF (for 20 ng/ml final concentration) or EGF (for 0.1 ng/ml final concentration) was added to each well as appropriate and the cells incubated with the IGF or EGF for 5 minutes at 37° C. The medium was removed (by pipetting) and then 100 μl of 2× Laemmli buffer was added. The plates were stored at 4° C. until the cells were harvested. (Harvesting should occur within 2 hours following addition of Laemmli buffer to the cells.)

To harvest the cells, a pipette was used to repeatedly draw up and expel the Laemmli buffer/cell mix and transfer into a 1.5 ml Eppendorf tube. The harvested cell lysates were kept at −20° C. until required. The protein concentration of each lysate could be determined using the DC protein assay kit (Bio-Rad Laboratories, USA, according to manufacturer's instructions).

Western Blot Technique

Cell samples were made up with 4× sample buffer, syringed with a 21 gauge needle and boiled for 5 minutes. Samples were loaded at equal volumes and a molecular weight ladder on 4-12% Bis-Tris gels (Invitrogen BV, The Netherlands) and the gels were run in an Xcell SureLock™ Mini-Cell apparatus (Invitrogen) with the solutions provided and according to the manufacturer's instructions. The gels were blotted onto Hybond C Extra™ membrane (Amersham Pharmacia Biotech UK Ltd.) for 1 hour at 30 volts in the Xcell SureLock™ Mini-Cell apparatus, using Western transfer buffer. The blotted membranes were stained with 0.1% Ponceau S to visualise transferred proteins and then cut into strips horizontally for multiple antibody incubations according to the molecular weight standards. Separate strips were used for detection of IGF-1R, Akt, MAPK and actin control.

The membranes were blocked for 1 hour at room temperature in PBST+5% milk solution. The membranes were then placed into 3 ml primary antibody solution in 4 well plates and the plates were incubated overnight at 4° C. The membranes were washed in 5 ml PBST, 3 times for 5 minutes each wash. The HRP-conjugated secondary antibody solution was prepared and 5 ml was added per membrane. The membranes were incubated for 1 hour at room temperature with agitation. The membranes were washed in 5 ml PBST, 3 times for 5 minutes each wash. The ECL solution (SuperSignal ECL, Pierce, Perbio Science UK Ltd) was prepared and incubated with the membranes for 1 minute (according to manufacturer's instructions), followed by exposure to light sensitive film and development.

The compounds of the Examples were found to have an IC$_{50}$ in the above test of less than 20 μM.

The invention claimed is:

1. A compound of formula (I):

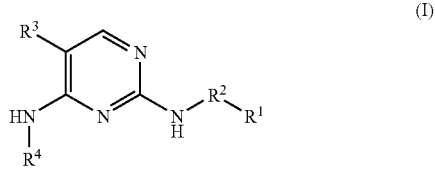

wherein

R$^1$ represents a 5- or 6-membered heteroaromatic ring comprising at least one ring heteroatom selected from nitrogen, oxygen, and sulphur, the ring being optionally substituted with at least one substituent selected from C$_1$-C$_6$alkyl, C$_1$-C$_6$alkoxy (each of which may be optionally substituted by at least one substituent selected from halogen, amino, hydroxyl, and trifluoromethyl), halogen, nitro, cyano, —NR$^5$R$^6$, carboxyl, hydroxyl, C$_2$-C$_6$alkenyl, C$_3$-C$_6$cycloalkyl, C$_1$-C$_6$alkoxycarbonyl, C$_1$-C$_6$alkylcarbonyl, C$_1$-C$_6$alkylcarbonylamino, phenylcarbonyl, —S(O)$_m$C$_1$-C$_6$alkyl, —C(O)NR$^7$R$^8$, —SO$_2$NR$^{7a}$R$^{8a}$, and an unsaturated 5- to 6-membered ring which may comprise at least one ring heteroatom selected from nitrogen, oxygen, and sulphur, the ring itself being optionally substituted with at least one substituent selected from C$_1$-C$_6$alkyl, C$_1$-C$_6$alkoxy (each of which may be optionally substituted by at least one substituent selected from halogen, amino, hydroxyl, and trifluoromethyl), halogen, nitro, cyano, —NR$^9$R$^{10}$, carboxyl, hydroxyl, C$_2$-C$_6$alkenyl, C$_3$-C$_6$cycloalkyl, C$_1$-C$_6$alkoxycarbonyl, C$_1$-C$_6$alkylcarbonyl, C$_1$-C$_6$alkylcarbonylamino, phenylcarbonyl, —S(O)$_n$ C$_1$-C$_6$alkyl, —C(O)NR$^{11}$R$^{12}$, and —SO$_2$NR$^{11a}$R$^{12a}$;

m is 0, 1, or 2;

n is 0, 1, or 2;

R$^2$ represents a C$_1$-C$_4$alkyl group optionally substituted with at least one substituent selected from halogen, hydroxyl, and C$_1$-C$_3$alkoxy;

R$^3$ represents halogen;

R$^4$ represents a 5-membered heteroaromatic ring comprising at least one ring heteroatom selected from nitrogen, oxygen, and sulphur, the ring being optionally substituted with at least one substituent selected from C$_1$-C$_6$alkyl, C$_1$-C$_6$alkoxy (each of which may be optionally substituted by at least one substituent selected from halogen, amino, hydroxyl, and trifluoromethyl), halogen, nitro, cyano, —NR$^{13}$R$^{14}$, carboxyl, hydroxyl, C$_2$-C$_6$alkenyl, C$_3$-C$_6$cycloalkyl, C$_1$-C$_4$ alkoxycarbonyl, C$_1$-C$_4$alkylcarbonyl, C$_1$-C$_4$alkylcarbonylamino, phenylcarbonyl, —S(O)$_p$C$_1$-C$_4$alkyl, —C(O)NR$^{15}$R$^{16}$, and —SO$_2$NR$^{15a}$R$^{16a}$;

p is 0, 1, or 2;

R$^5$ and R$^6$ each independently represent hydrogen, C$_1$-C$_4$alkyl, or C$_3$-C$_6$cycloalkyl, or R$^5$ and R$^6$ together with the nitrogen atom to which they are attached form a 4- to 6-membered saturated heterocycle;

R$^7$ and R$^8$ each independently represent hydrogen, C$_1$-C$_4$alkyl, or C$_3$-C$_6$cycloalkyl, or R$^7$ and R$^8$ together with the nitrogen atom to which they are attached form a 4- to 6-membered saturated heterocycle;

R$^{7a}$ and R$^{8a}$ each independently represent hydrogen, C$_1$-C$_4$alkyl, or C$_3$-C$_6$cycloalkyl, or R$^{7a}$ and R$^{8a}$ together with the nitrogen atom to which they are attached form a 4- to 6-membered saturated heterocycle;

R$^9$ and R$^{10}$ each independently represent hydrogen, C$_1$-C$_4$alkyl, or C$_3$-C$_6$cycloalkyl, or R$^9$ and R$^{10}$ together with the nitrogen atom to which they are attached form a 4- to 6-membered saturated heterocycle;

R$^{11}$ and R$^{12}$ each independently represent hydrogen, C$_1$-C$_4$alkyl, or C$_3$-C$_6$cycloalkyl, or R$^{11}$ and R$^{12}$ together with the nitrogen atom to which they are attached form a 4- to 6-membered saturated heterocycle;

R$^{11a}$ and R$^{12a}$ each independently represent hydrogen, C$_1$-C$_4$alkyl, or C$_3$-C$_6$cycloalkyl, or R$^{11a}$ and R$^{12a}$ together with the nitrogen atom to which they are attached form a 4- to 6-membered saturated heterocycle;

R$^{13}$ and R$^{14}$ each independently represent hydrogen, C$_1$-C$_4$alkyl, or C$_3$-C$_6$cycloalkyl, or R$^{13}$ and R$^{14}$ together with the nitrogen atom to which they are attached form a 4- to 6-membered saturated heterocycle;

R$^{15}$ and R$^{16}$ each independently represent hydrogen, C$_1$-C$_4$alkyl, or C$_3$-C$_6$cycloalkyl, or R$^{15}$ and R$^{16}$ together with the nitrogen atom to which they are attached form a 4- to 6-membered saturated heterocycle; and R$^{15a}$ and R$^{16a}$ each independently represent hydrogen, C$_1$-C$_4$alkyl, or C$_3$-C$_6$cycloalkyl, or R$^{15a}$ and R$^{16a}$ together with the nitrogen atom to which they are attached form a 4- to 6-membered saturated heterocycle;

or a pharmaceutically acceptable salt thereof.

2. A compound according to claim 1, wherein R$^1$ represents a 5- or 6-membered heteroaromatic ring comprising at least one ring heteroatom selected from nitrogen, oxygen, and sulphur, the ring being optionally substituted with at least one substituent selected from C$_1$-C$_6$alkyl, C$_1$-C$_6$alkoxy (each of which may be optionally substituted with at least one hydroxyl), halogen, —C(O)NR$^7$R$^8$, C$_1$-C$_6$alkoxycarbonyl, and an unsaturated 5- to 6-membered ring which may comprise at least one ring heteroatom selected from nitrogen and oxygen, the ring itself being optionally substituted with at least one substituent selected from C$_1$-C$_6$alkyl, C$_1$-C$_6$alkoxy (each of which may be optionally substituted by at least one halogen), halogen, and cyano, R$^7$ and R$^8$ are both hydrogen, or R$^7$ and R8 together with the nitrogen atom to which they are attached form a 4- to 6-membered saturated heterocycle, or a pharmaceutically acceptable salt thereof.

3. A compound according to claim 1, wherein R$^1$ represents pyridyl, imidazolyl, isoxazolyl, pyrazolyl, furyl, pyrazinyl, pyridazinyl, pyrimidinyl, pyrrolyl, or thienyl said pyridyl, imidazolyl, isoxazolyl, pyrazolyl, furyl, pyrazinyl, pyridazinyl, pyrimidinyl, pyrrolyl, or thienyl being optionally substituted with at least one substituent selected from methyl, isopropyl, hydroxymethyl, methoxy, chloro, bromo, carbamoyl, methoxycarbonyl, pyrrolidin-1-ylcarbonyl, phenyl, and pyridyl said phenyl or pyridyl being optionally substituted with at least one substituent selected from methyl, trifluoromethyl, methoxy, ethoxy, trifluoromethoxy, fluoro, chioro, bromo, and cyano, or a pharmaceutically acceptable salt thereof.

4. A compound according to claim 1, wherein R$^2$ represents a C$_1$-C$_4$alkyl group, or a pharmaceutically acceptable salt thereof.

5. A compound according to claim 1, wherein, R$^4$ represents a 5-membered heteroaromatic ring comprising at least one nitrogen, the ring being optionally substituted with at least one substituent selected from C$_1$-C$_6$alkyl and C$_3$-C$_6$cycloalkyl, or a pharmaceutically acceptable salt thereof.

6. A compound according to claim 5, wherein R$^4$ is pyrazolyl optionally substituted with at least one substituent selected from methyl, ethyl, isopropyl, propyl, t-butyl, and cyclopropyl, or a pharmaceutically acceptable salt thereof.

7. A compound according to claim 1, wherein

R$^1$ is selected from pyrid-2-yl, pyrid-3-yl, pyrid-4-yl, 2-methoxypyrid-5-yl, 2-cyanopyrid-5-yl, 3-bromopyrid-5-yl, 3-(pyrid-2-yl)pyrid-5-yl, 4-(pyrid-2-yl)pyrid-2-yl, 3-chloropyrid-2-yl, 3-methylpyrid-2-yl, 6-methylpyrid-2-yl, 5,6-dimethylpyrid-2-yl, imidazol-4-yl, imidazol-5-yl, 3-methylisoxazol-5-yl, 5-methylisoxazol-3-yl, 3-isopropylisoxazol-5-yl, 3-methoxycarbonylisoxazol-5-yl, 3-(hydroxymethyl)isoxazol-5-yl, 3-carbamoylisoxazol-5-yl, 3-(pyrrolidin-1-ylcarbonyl)isoxazol-5-yl, 3-phenylisoxazol-5-yl, 3-(pyrid-2-yl)isoxazol-5-yl, 3-(2-methoxypyrid-3-yl)isoxazol-5-yl, 3-(2-methoxyphenyl)isoxazol-5-yl, 3-(3-methoxyphenyl)isoxazol-5-yl, 3-(2-ethoxyphenyl)isoxazol-5-yl, 3-(2-trifluoromethylphenyl)isoxazol-5-yl, 3-(2-trifluoromethoxyphenyl)isoxazol-5-yl, 3-(2-chlorophenyl)isoxazol-5-yl, 3-(2-bromophenyl)isoxazol-5-yl, 3-(2-methylphenyl)isoxazol-5-yl, 3-(2-fluorophenyl)isoxazol-5-yl, 3-(2-cyanophenyl)isoxazol-5-yl, 5-methylpyrazol-4-yl, fur-2-yl, fur-3-yl, 5-methylfur-2-yl, pyrazin-2-yl, 2-methylpyrazin-5-yl, pyridazin-3-yl, pyrimidin-4-yl, 1-methylpyrrol-2-yl, and thien-3-yl;

R$^2$ is selected from methyl, ethyl, and propyl;

R$^3$ represents chloro, or bromo; and

R⁴ is selected from 5-methylpyrazol-3-yl, 5-ethylpyrazol-3-yl, 5-isopropylpyrazol-3-yl, 5-propylpyrazol-3-yl, 5-t-butylpyrazol-3-yl, and 5-cyclopropylpyrazol-3-yl;

or a pharmaceutically acceptable salt thereof.

8. A compound selected from:
5-Bromo-2-(3-methylisoxazol-5-ylmethylamino)-4-(5-cyclopropyl- 1H-pyrazol-3-ylamino)pyrimidine;
5-Chloro-2-(3-phenylisoxazol-5-ylmethylamino)-4-(5-methyl-1H-pyrazol-3-ylamino)pyrimidine,
5-Chloro-2-(3-pyrid-2-ylisoxazol-5-ylmethylamino)-4-(5-methyl-1H-pyrazol-3-ylamino)pyrimidine;
5-Bromo-2-(3-pyrid-2-ylisoxazol-5-ylmethylamino)-4-(5-methyl-1H-pyrazol-3-ylamino)pyrimidine;
5-Chloro-2-(3-methylisoxazol-5-ylmethylamino)-4-(5-tert-butyl- 1H-pyrazol-3-ylamino)pyrimidine;
5-Bromo-2-(3-methylisoxazol-5-ylmethylamino)-4-(5-ethyl-1H-pyrazol-3-ylamino)pyrimidine;
5-Chloro-2-[3-(2-fluorophenyl)isoxazol-5-ylmethylamino]-4-(5-methyl-1H-pyrazol-3-ylamino)pyrimidine;
5-Bromo-2-[3-(2-fluorophenyl)isoxazol-5-ylmethylamino]-4-(5-methyl-1H-pyrazol-3-ylamino)pyrimidine;
5-Chloro-2-[3-(2-fluorophenyl)isoxazol-5-ylmethylamino]-4-(5-tert-butyl-1H-pyrazol-3-ylamino)pyrimidine;
5-Bromo-4-(5-isopropyl-1H-pyrazol-3-ylamino)-2-(pyrid-2-ylmethylamino) pyrimidine;
5-Bromo-2-(3-methylisoxazol-5-ylmethylamino)-4-(5-propyl-1H-pyrazol-3-ylamino)pyrimidine;
5-Bromo-2-(3-methylisoxazol-5-ylmethylamino)-4-(5-isopropyl- 1H-pyrazol-3-ylamino)pyrimidine;
5-Chloro-2-[3-(pyrid-2-yl)isoxazol-5-ylmethylamino]-4-(5-tert-butyl- 1H-pyrazol-3-ylamino)pyrimidine;
5-Bromo-2-[3-(pyrid-2-yl)isoxazol-5-ylmethylamino]-4-(5-tert-butyl- 1H-pyrazol-3-ylamino)pyrimidine; and
5-Bromo-2-(3-bromopyrid-5-ylmethylamino)-4-(5-tert-butyl- 1H-pyrazol-3-ylamino)pyrimidine;

or a pharmaceutically acceptable salt thereof.

9. A process for the preparation of a compound according to claim 1, which comprises:
(i) reacting a compound of formula (II)

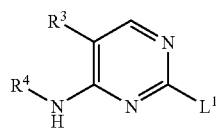

(II)

wherein L¹ represents a leaving group and R³ and R⁴ are as defined in claim 1, with a compound of formula (III), H₂N—R²—R¹, wherein R¹ and R² are as defined in claim 1; or (ii) reacting a compound of formula (IV)

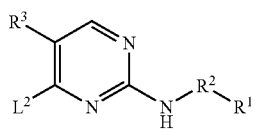

(IV)

wherein L² represents a leaving group and R¹, R², and R³ are as defined in claim 1, with a compound of formula (V), H₂N—R⁴, wherein R⁴ is as defined in claim 1; or (iii) reacting a compound of formula (VI)

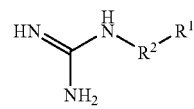

(VI)

wherein R¹ and R² are as defined in claim 1, with a compound of formula (VII)

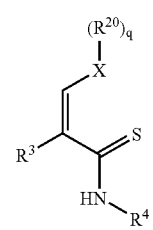

(VII)

wherein X represents an oxygen atom and q is 1, or X represents a nitrogen atom and q is 2, each R²⁰ independently represents a C₁-C₆alkyl group, and R³ and R⁴ are as defined in claim 1; or (iv) when R⁴ represents a substituted pyrazolyl, reacting a compound of formula (VIII)

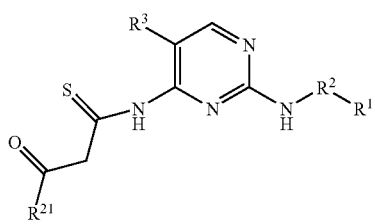

(VIII)

wherein R²¹ represents a C₁-C₆alkyl or C₃-C₆cycloalkyl group and R¹, R², and R³ are as defined in claim 1 with hydrazine;

and optionally thereafter carrying out one or more of the following:

converting the compound obtained to a further compound according to claim 1 forming a pharmaceutically acceptable salt of the compound.

10. A pharmaceutical composition comprising a compound of claim 1, or a pharmaceutically acceptable salt thereof in association with a pharmaceutically acceptable adjuvant, diluent, or carrier.

11. A process for the preparation of a pharmaceutical composition of claim 10, which comprises mixing a compound of formula (I), or a pharmaceutically acceptable salt thereof with a pharmaceutically acceptable adjuvant, diluent, or carrier.

12. A method of treating cancer, which comprises administering to a patient-a compound of claim 1, or a pharmaceutically acceptable salt thereof
wherein said cancer is selected from breast, prostate, and colon cancer.

13. A compound according to claim 1, wherein $R^1$ is a 5-or 6-membered heteroaromatic ring selected from thienyl, pyrazolyl, isoxazolyl, thiadiazolyl, pyrrolyl, furanyl, thiazolyl, triazolyl, tetrazolyl, imidazolyl, pyrazinyl, pyridazinyl, pyrimidinyl, and pyridyl, or a pharmaceutically acceptable salt thereof.

14. A compound according to claim 1, wherein $R^1$ is a 5-or 6-membered heteroaromatic ring selected from thienyl, pyrazolyl, isoxazolyl, thiadiazolyl, pyrrolyl, furanyl, thiazolyl, triazolyl, tetrazolyl, imidazolyl, pyrazinyl, and pyridyl, or a pharmaceutically acceptable salt thereof.

15. A compound according to claim 1, wherein, in $R^1$ said unsaturated 5- to 6-membered ring is selected from phenyl, cylopentenyl, cyclohexenyl, thienyl, pyrazolyl, isoxazolyl, thiadiazolyl, pyrrolyl, furanyl, thiazolyl, triazolyl, tetrazolyl, imidazolyl, pyrazinyl, pyridazinyl, pyrimidinyl, and pyridyl, or a pharmaceutically acceptable salt thereof.

16. A compound according to claim 1, wherein, in $R^1$ said unsaturated 5- to 6-membered ring is selected from phenyl, cylopentenyl, cyclohexenyl, thienyl, pyrazolyl, isoxazolyl, thiadiazolyl, pyrrolyl, furanyl, thiazolyl, triazolyl, tetrazolyl, imidazolyl, pyrazinyl, and pyridyl, or a pharmaceutically acceptable salt thereof.

17. A compound according to claim 1, wherein $R^4$ is a 5-membered heteroaromatic ring selected from thienyl, pyrazolyl, isoxazolyl, thiadiazolyl, pyrrolyl, furanyl, thiazolyl, triazolyl, tetrazolyl, and imidazolyl, or a pharmaceutically acceptable salt thereof.

18. A compound according to claim 1, wherein $R^4$ is pyrazolyl, or a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 7,521,453 B2 | Page 1 of 1 |
| APPLICATION NO. | : 10/497744 | |
| DATED | : April 21, 2009 | |
| INVENTOR(S) | : Barlaam et al. | |

It is certified that error appears in the above-identified patent and that said Letters Patent is hereby corrected as shown below:

On the Title Page

Item [*] Notice: Subject to any disclaimer, the term of this patent is extended or adjusted under 35 USC 154(b) by 542 days Delete the phrase "by 542 days" and insert -- by 832 days --

Signed and Sealed this

Fourth Day of May, 2010

David J. Kappos
*Director of the United States Patent and Trademark Office*